(12) United States Patent
Hendriks

(10) Patent No.: US 7,767,652 B2
(45) Date of Patent: Aug. 3, 2010

(54) MEDICAL DEVICES AND METHODS FOR REDUCING LOCALIZED FIBROSIS

(75) Inventor: Marc Hendriks, Brussum (NL)

(73) Assignee: Medtronic, Inc., Minneapolis, MN (US)

( * ) Notice: Subject to any disclaimer, the term of this patent is extended or adjusted under 35 U.S.C. 154(b) by 874 days.

(21) Appl. No.: 11/183,485

(22) Filed: Jul. 18, 2005

(65) Prior Publication Data

US 2006/0029636 A1 Feb. 9, 2006

Related U.S. Application Data

(60) Provisional application No. 60/589,700, filed on Jul. 21, 2004.

(51) Int. Cl.
*A61K 31/70* (2006.01)
*C07H 21/04* (2006.01)
(52) U.S. Cl. .................. 514/44; 536/24.5; 977/931
(58) Field of Classification Search ................. None
See application file for complete search history.

(56) References Cited

U.S. PATENT DOCUMENTS

| | | | |
|---|---|---|---|
| 4,997,643 A | 3/1991 | Partain, III et al. | |
| 5,140,103 A | 8/1992 | Eyre | |
| 5,300,434 A | 4/1994 | Eyre | |
| 5,320,970 A | 6/1994 | Eyre | |
| 5,328,913 A | 7/1994 | Murad et al. | |
| 5,455,179 A | 10/1995 | Eyre | |
| 5,473,052 A | 12/1995 | Eyre | |
| 5,518,730 A | 5/1996 | Fuisz | |
| 5,532,169 A | 7/1996 | Eyre | |
| 5,576,189 A | 11/1996 | Eyre | |
| 5,641,687 A | 6/1997 | Eyre | |
| 5,641,837 A | 6/1997 | Eyre | |
| 5,652,112 A | 7/1997 | Eyre | |
| 5,656,439 A | 8/1997 | Eyre | |
| 5,677,198 A | 10/1997 | Eyre | |
| 5,702,909 A | 12/1997 | Eyre | |
| 5,834,014 A | 11/1998 | Weiner et al. | |
| 5,834,221 A | 11/1998 | Eyre | |
| 5,840,293 A | 11/1998 | Nacht et al. | |
| 5,919,634 A | 7/1999 | Eyre | |
| 5,939,274 A | 8/1999 | Eyre | |
| 5,939,485 A | 8/1999 | Bromberg et al. | |
| 5,955,109 A | 9/1999 | Won et al. | |
| 5,962,427 A | 10/1999 | Goldstein et al. | |
| 5,962,639 A | 10/1999 | Eyre | |
| 6,010,862 A | 1/2000 | Eyre | |
| 6,027,903 A | 2/2000 | Eyre | |
| 6,048,705 A | 4/2000 | Eyre | |
| 6,100,379 A | 8/2000 | Eyre | |
| 6,132,976 A | 10/2000 | Poole et al. | |
| 6,143,037 A * | 11/2000 | Goldstein et al. ........... 424/422 | |
| 6,143,511 A | 11/2000 | Eyre | |
| 6,153,732 A | 11/2000 | Eyre | |
| 6,174,917 B1 | 1/2001 | McLean | |
| 6,190,896 B1 | 2/2001 | Fraij | |
| 6,207,178 B1 | 3/2001 | Westesen et al. | |
| 6,248,345 B1 | 6/2001 | Goldenheim et al. | |
| 6,451,335 B1 | 9/2002 | Goldenheim et al. | |
| 6,484,565 B2 | 11/2002 | Shin et al. | |
| 7,056,704 B2 * | 6/2006 | Tuschl et al. ............ 435/91.1 |
| 2003/0219852 A1 * | 11/2003 | Bank et al. ............. 435/68.1 |
| 2005/0143817 A1 * | 6/2005 | Hunter et al. ........... 623/11.11 |
| 2005/0255487 A1 * | 11/2005 | Khvorova et al. ............ 435/6 |
| 2006/0030538 A1 | 2/2006 | Hendriks | |

FOREIGN PATENT DOCUMENTS

| | | | |
|---|---|---|---|
| DE | 20302861 | * | 8/2003 |
| EP | 0502928 | | 1/1996 |
| EP | 0682257 | | 4/1999 |
| EP | 1088564 A1 | | 4/2001 |
| EP | 1375510 A1 | | 1/2004 |
| EP | 0682256 | | 10/2004 |
| JP | 2000-143539 | | 5/2000 |
| WO | WO 91/08478 | | 6/1991 |
| WO | WO 92/03123 | | 3/1992 |
| WO | WO 98/18610 | | 5/1998 |
| WO | WO 98/41865 | | 9/1998 |
| WO | WO 99/38507 | | 8/1999 |
| WO | WO 02/06373 | | 1/2002 |
| WO | WO 02/011698 | | 2/2002 |
| WO | WO 2004/073731 | | 9/2004 |
| WO | WO 2006/002031 A2 | | 4/2006 |
| WO | WO 2006/002031 A3 | | 4/2006 |

OTHER PUBLICATIONS

Elbashir et al (Methods, 2002, 26:199-213).*
Valtavaara er al (J. Biol. Chem. 272(11):6831-6834, 1997).*
Opalinska et al., "Nucleic-Acid Therapeutics: Basic Principles and Recent Applications" *Nature Reviews Drug Discovery*, Jul. 2002; 1:503-514.
Schmidt, "Negotiating the RNAi Patent Thicket" *Nature Biotechnology*, Mar. 2007; 25(3):273-275.
Kitabwalla, et al., "RNA interference—a new weapon against HIV and beyond" *N Engl J Med*, Oct. 24, 2002;347(17):1364-1367.
Xu et al., "Effective small interfering RNAs and phosphorothioate antisense DNAs have different preferences for target sites in the luciferase mRNAs" *Biochem Biophys Res Comm*, 2003;306:712-717.

(Continued)

*Primary Examiner*—Richard Schnizer
(74) *Attorney, Agent, or Firm*—Mueting, Raasch & Gebhardt, P.A.

(57) ABSTRACT

Medical devices and methods for reducing localized fibrosis at the site of the medical device.

16 Claims, 9 Drawing Sheets

OTHER PUBLICATIONS

Kretschmer-Kazemi Far et al. "The activity of siRNA in mammalian cells is related to structural target accessibility: a comparison with antisense oligonucleotids" *Nucleic Acids Research*, Aug. 1, 2003;31(15):4417-4424.

Xu et al,. "Functional comparison of single- and double-stranded siRNAs in mammalian cells" *Biochem Biophys Res Comm.*, Apr. 9, 2004;316(3):680-687.

Alexakis et al., "Structurally different RGTAs modulate collagen-type expression by cultured aortic smooth muscle cells via different pathways involving fibroblast growth factor-2 or transforming growth factor-β1", *FASEB J*, Jul. 2004;18(10):1147-1149.

Anderson, "Chapter 4, Mechanisms of inflammation and infection with implanted devices", *Cardiovasc Pathol*, Jul.-Sep. 1993;2(3)Suppl:33S-41S.

Bailey, et al., "Characterization of the collagen of human hypertrophic and normal scars", *Biochim Biophys Acta*, Oct. 20, 1975;405(2):412-421.

Bank et al., "Defective collagen crosslinking in bone, but not in ligament or cartilage, in Bruck syndrome: indications for a bone-specific telopeptide lysyl hydroxylase on chromosome 17", *Proc Nail Acad Sci USA*, Feb. 2, 1999;96(3):1054-1058.

Bank, et al., "Sensitive fluorimetric quantitation of pyridinium and pentosidine crosslinks in biological samples in a single high-performance liquid chromatographic run", *J Chromatogr B*, Dec. 5, 1997;703(1-2):37-44.

Barnes et al., "Age-related variations in hydroxylation of lysine and proline in collagen", *Biochem J*, May 1974; 139(2):461-468.

Beer et al., "Glucocorticoid-regulated gene expression during cutaneous wound repair", *Vitam Horm*, 2000;59:217-239.

Bernstein et al., "Role for a bidentate ribonuclease in the initiation step of RNA interference", *Nature*, Jan 18, 2001;409(6818):363-366.

Bonadio et al., "Localized, direct plasmid gene delivery in vivo: prolonged therapy results in reproducible tissue regeneration", *Nat Med*, Jul. 1999;5(7):753-759.

Brinckmann et al., "Overhydroxylation of lysyl residues is the initial step for altered collagen cross-links and fibril architecture in fibrotic skin", *J Invest Dermatol*, Oct. 1999;113(4):617-621.

Caplen et al., "Specific inhibition of gene expression by small double-stranded RNAs in invertebrate and vertebrate systems", *Proc Natl Acad Sci USA*, Aug. 14, 2001;98(17):9742-9747.

Elbashir et al., "Duplexes of 21-nucleotide RNAs mediate RNA interference in cultured mammalian cells", *Nature*, May 24, 2001;411(6836):494-498.

Elbashir et al., "Functional anatomy of siRNAs for mediating efficient RNAi in *Drosophila melanogaster* embryo lysate", *EMBO J*, Dec. 3, 2001;20(23):6877-6888.

Elek et al., "The virulence of *Staphylococcus pyogenes* for man; a study of the problems of wound infection", *Br J Exp Pathol*, Dec. 1957;38(6):573-586.

"First Strand cDNA Synthesis Kit for RT-PCR (AMV)" datasheet. Roche Applied Science, Indianapolis, IN, 2004. [Retrieved on Sep. 23, 2005]. Retrieved from the Internet:<URL:http://www.roche-applied-science.com/pack-insert/1483188a.pdf>; 4 pgs.

Gerriets et al., "Lung collagen cross-links in rats with experimentally induced pulmonary fibrosis", *Biochim Biophys Acta*, Jun. 7, 1996;1316(2):121-131.

Hammond et al., "Post-transcriptional gene silencing by double-stranded RNA", *Nat Rev Genet*, Feb. 2001;2(2):110-119.

Hannon, "RNA interference", *Nature*, Jul. 11, 2002;418(6894):244-251.

Hautala et al, "Minoxidil specifically decreases the expression of lysine hydroxylase in cultured human skin fibroblasts", *Biochem J*, Apr. 1, 1992;283:51-54.

Holen et al, "Positional effects of short interfering RNAs targeting the human coagulation trigger Tissue Factor", *Nucleic Acids Res*, Apr. 15, 2002;30(8):1757-1766.

Hutvagner et al., "RNAi: nature abhors a double-strand", *Curr Opin Genet Dev*, Apr. 2002; 12(2):225-232.

Kagan, "Intra- and extracellular enzymes of collagen biosynthesis as biological and chemical targets in the control of fibrosis", *Acta Trop*, Oct. 23, 2000;77(1):147-152.

Knott et al., "Chemistry of collagen cross-linking: biochemical changes in collagen during the partial mineralization of turkey leg tendon", *Biochem J*, Mar. 1, 1997;322(Pt 2):535-542.

Kurreck, "Antisense technologies: Improvement through novel chemical modifications", *Eur J Biochem*, Apr. 2003;270(8):1628-1644.

Kyriakides et al., "Regulation of Angiogenesis and Matrix Remodeling by Localized, Matrix-Mediated Antisense Gene Delivery", *Molecular Therapy*, Jun. 2001;3(6):842-849.

Murad et al., "Suppression of fibroblast proliferation and lysyl hydroxylase activity by minoxidil", *J Biol Chem*, Sep. 5, 1987;262(25):11973-11978.

Murad et al., "Minimum Structural Requirements for Minoxidil Inhibition of Lysyl Hydroxylase in Cultured Fibroblasts", *Arch Biochem Biophys*, Jan. 1994;308(1):42-47.

Myers et al, "Extraction of implanted transvenous pacing leads: a review of a persistent clinical problem", *Am Heart J*, Mar. 1991;121(3 Pt 1):881-888.

National Center for Biotechnology Information, National Library of Medicine, National Institutes of Health, GenBank Locus AF283255, Accession No. AF283255, "*Mus musculus* pro-collagen lysyl hydroxylase 2 (Plod2) gene, promoter and partial cds", [online]. Bethesda, MD [retrieved on Sep. 8, 2005]. Retrieved from the Internet: <URL:http://www.ncbi.nlm.nih.gov/entrez/viewer.fcgi?db=nucleotide&val=1266 7200; 2 pgs.

National Center for Biotechnology Information, National Library of Medicine, National Institutes of Health, GenBank Locus RNO430860, Accession No. AJ430860, "*Rattus norvegicus* mRNA for procollagen-lysine, 2-oxoglutarate 5-dioxygenase 2, long variant (plod2 gene)", [online]. Bethesda, MD [retrieved on Sep. 8, 2005]. Retrieved from the Internet: <URL:http://www.ncbi.nlm.nih.gov/entrez/viewer.fcgi?db=nucleotide&val=2840 0780; 3 pgs.

National Center for Biotechnology Information, National Library of Medicine, National Institutes of Health, GenBank Locus RNO430861, Accession No. AJ430861, "*Rattus norvegicus* mRNA for procollagen-lysine, 2-oxoglutarate 5-dioxygenase 2, short variant, (plod2 gene)", [online]. Bethesda, MD [retrieved on Sep. 8, 2005]. Retrieved from the Internet: <URL:http://www.ncbi.nlm.nih.gov/entrez/viewer.fcgi?db=nucleotide&val=2840 0782; 3 pgs.

National Center for Biotechnology Information, National Library of Medicine, National Institutes of Health, GenBank Locus AY026758S2, Accession No. AY026756, "*Mus musculus* lysyl hydroxylase 2 (Plod2) gene, exon 13A and partial cds", [online]. Bethesda, MD [retrieved on Sep. 8, 2005]. Retrieved from the Internet: <URL:http://www.ncbi.nlm.nih.gov/entrez/viewer.fcgi?db=nucleotide&val=1514 5787; 2 pgs.

National Center for Biotechnology Information, National Library of Medicine, National Institutes of Health, GenBank Locus AY026757, Accession No. AY026757, "*Homo sapiens* lysyl hydroxylase 2 (PLOD2) gene, exon 13a and partial cds", [online]. Bethesda, MD [retrieved on Sep. 8, 2005]. Retrieved from the Internet: <URL:http://www.ncbi.nlm.nih.gov/entrez/viewer.fcgi ?db=nucleotide&val=1514 5783; 2 pgs.

National Center for Biotechnology Information, National Library of Medicine, National Institutes of Health, GenBank Locus AY026758S1, Accession No. AY026758, "*Mus musculus* lysyl hydroxylase 2 (Plod2) gene, exon 1 and partial cds", [online]. Bethesda, MD [retrieved on Sep. 8, 2005]. Retrieved from the Internet: <URL:http://www.ncbi.nlm.nih.gov/entrez/viewer.fcgi?db=nucleotide&val=1514 5785; 4 pgs.

National Center for Biotechnology Information, National Library of Medicine, National Institutes of Health, GenBank Locus AY026758S1, Accession No. AY026758, "*Mus musculus* lysyl hydroxylase 2 (Plod2) gene, exon 1 and partial cds", [online]. Bethesda, MD [retrieved on Sep. 8, 2005]. Retrieved from the Internet: <URL:http://www.ncbi.nlm.nih.gov/entrez/viewer.fcgi?db=nucleotide&val=1514 5786; 2 pgs.

National Center for Biotechnology Information, National Library of Medicine, National Institutes of Health, GenBank Locus AY399885, Accession No. AY399885, "*Homo sapiens* PLOD2 gene, Virtual Transcript, partial sequence, genomic survey sequence", [online]. Bethesda, MD [retrieved on Sep. 8, 2005]. Retrieved from the Internet: <URL:http://www.ncbi.nlm.nih.gov/entrez/viewer.fcgi?db=nucleotide&val=3975 5874; 2 pgs.

National Center for Biotechnology Information, National Library of Medicine, National Institutes of Health, GenBank Locus AY399886, Accession No. AY399886, "Pan troglodytes PLOD2 gene, Virtual Transcript, partial sequence, genomic survey sequence", [online]. Bethesda, MD [retrieved on Sep. 8, 2005]. Retrieved from the Internet: <URL:http://www.ncbi.nlm.nih.gov/entrez/viewer.fcgi?db=nucleotide&val=3975 5875; 2 pgs.

National Center for Biotechnology Information, National Library of Medicine, National Institutes of Health, GenBank Locus AY399887, Accession No. AY399887, "*Mus musculus* PLOD2 gene, Virtual Transcript, partial sequence, genomic survey sequence", [online]. Bethesda, MD [retrieved on Sep. 8, 2005]. Retrieved from the Internet: <URL:http://www.ncbi.nlm.nih.gov/entrez/viewer.fcgi?db=nucleotide&val=3975 5876; 2 pgs.

National Center for Biotechnology Information, National Library of Medicine, National Institutes of Health, GenBank Locus BC016834, Accession No. BC016834, "*Homo sapiens* procollagen-lysine, 2-oxoglutarate 5-dioxygenase 2, mRNA (cDNA clone Image:3883264), partial cds", [online]. Bethesda, MD [retrieved on Sep. 8, 2005]. Retrieved from the Internet: <URL:http://www.ncbi.nlm.nih.gov/entrez/viewer.fcgi?db=nucleotide&val=1687 7123; 3 pgs.

National Center for Biotechnology Information, National Library of Medicine, National Institutes of Health, GenBank Locus BC021352, Accession No. BC021352, "*Mus musculus* procallagen lysine, 2-oxoglutarate 5-diosygenase 2, mRNA (cDNA clone MGC:29312 Image:5007509), complete cds", [online]. Bethesda, MD [retrieved on Sep. 8, 2005]. Retrieved from the Internet<URL:http://www.ncbi.nlm.nih.gov/entrez/viewer.fcgi?db=nucleotide&val=18204026; 4 pgs.

National Center for Biotechnology Information, National Library of Medicine, National Institutes of Health, GenBank Locus BC 037169, Accession No. BC037169, "*Homo sapiens* procollagen-lysine, 2-oxoglutarate 5-dioxygenase 2, transcript varient 1, mRNA (cDNA clone MGC:45324 Image:4994235), complete cds", [online]. Bethesda, MD [retrieved on Sep. 8, 2005]. Retrieved from the Internet: <URL:http://www.ncbi.nlm.nih.gov/entrez/viewer.fcgi?db=nucleotide&val=2271 3624; 4 pgs.

National Center for Biotechnology Information, National Library of Medicine, National Institutes of Health, GenBank Locus CN641549, Accession No. CN641549, "Illumigen MCQ 5004 Katze MMPL2 *Macaca mulatta* cDNA clone IBIUW:5830 5' similar to Bases 76 to 1036 highly similar to human PLOD2 (Hs.41270), mRNA sequence", [online]. Bethesda, MD [retrieved on Sep. 8, 2005]. Retrieved from the Internet: <URL:http://www.ncbi.nlm.nih.gov/entrez/viewer.fcgi?db=nucleotide&val=4715 2559; 2 pgs.

National Center for Biotechnology Information, National Library of Medicine, National Institutes of Health, GenBank Locus CN642656, Accession No. CN642656, "Illumigen MCQ 6695 Katze MMPL2 *Macaca mulatta* cDNA clone IBIUW:4556 5' similar to Bases 1 to 116 highly similar to human PLOD2 (Hs.41270), mRNA sequence", [online]. Bethesda, MD [retrieved on Sep. 8, 2005]. Retrieved from the Internet: <URL:http://www.ncbi.nlm.nih.gov/entrez/viewer.fcgi?db=nucleotide&val=4715 3666; 2 pgs.

National Center for Biotechnology Information, National Library of Medicine, National Institutes of Health, GenBank Locus CN646323 Accession No. CN646323, "Illumigen MCQ 26029 Katze MMBR *Macaca mulatta* cDNA clone IBIUW:8687 5' similar to Bases 158 to 1001 highly similar to human PLOD2 (Hs.41270), mRNA sequence", [online]. Bethesda, MD [retrieved on Sep. 8, 2005]. Retrieved from the Internet: <URL:http://www.ncbi.nlm.nih.gov/entrez/viewer.fcgi?db=nucleotide&val=4715 9766; 2 pgs.

National Center for Biotechnology Information, National Library of Medicine, National Institutes of Health, GenBank Locus CN803778, Accession No. CN803778, "Illumigen MCQ 33750 Katze MMPL1 *Macaca mulatta* cDNA clone IBIUW:12969 5' similar to Bases 1 to 542 highly similar to human PLOD2 (Hs.41270), mRNA sequence", [online]. Bethesda, MD [retrieved on Sep. 8, 2005]. Retrieved from the Internet: <URL:http://www.ncbi.nlm.nih.gov/entrez/viewer.fcgi?db=nucleotide&val=4769 9754; 2 pgs.

National Center for Biotechnology Information, National Library of Medicine, National Institutes of Health, GenBank Locus CO579544, Accession No. CO579544, "Illumigen MCQ 49992 Katze MMOV *Macaca mulatta* cDNA clone IBIUW:18341 5' similar to Bases 4 to 983 highly similar to human PLOD2 (Hs.41270), mRNA sequence", [online]. Bethesda, MD [retrieved on Sep. 8, 2005]. Retrieved from the Internet: <URL:http://www.ncbi.nlm.nih.gov/entrez/viewer.fcgi?db=nucleotide&val=5041 0506; 2 pgs.

National Center for Biotechnology Information, National Library of Medicine, National Institutes of Health, GenBank Locus CQ754901, Accession No. CQ754901, "Sequence 48 from Patent EP1375510", [online]. Bethesda, MD [retrieved on Sep. 8, 2005]. Retrieved from the Internet: <URL:http://www.ncbi.nlm.nih.gov/entrez/viewer.fcgi?db=nucleotide&val=4484 5929; 1 pg.

National Center for Biotechnology Information, National Library of Medicine, National Institutes of Health, GenBank Locus CQ754902, Accession No. CQ754902, "Sequence 49 from Patent EP1375510", [online]. Bethesda, MD [retrieved on Sep. 8, 2005]. Retrieved from the Internet: <URL:http://www.ncbi.nlm.nih.gov/entrez/viewer.fcgi?db=nucleotide&val=4484 5930; 1 pg.

National Center for Biotechnology Information, National Library of Medicine, National Institutes of Health, GenBank Locus CQ754905, Accession No. CQ754905, "Sequence 52 from Patent EP1375510", [online]. Bethesda, MD [retrieved on Sep. 8, 2005]. Retrieved from the Internet: <URL:http://www.ncbi.nlm.nih.gov/entrez/viewer.fcgi?db=nucleotide&val=4484 5933; 1 pg.

National Center for Biotechnology Information, National Library of Medicine, National Institutes of Health, GenBank Locus DN991618, Accession No. DN991618, "TC119547 Human adult whole brain, large insert, pCMV expression library *Homo sapiens* cDNA clone TC119547 5' similar to *Homo sapiens* procollagen-lysine, 2-oxoglutarate 5-dioxygenase 2 (PLOD2), transcript varient 2, mRNA sequence", [online]. Bethesda, MD [retrieved on Sep. 8, 2005]. Retrieved from the Internet: <URL:http://www.ncbi.nlm.nih.gov/entrez/viewer.fcgi?db=nucleotide&val=6625 1449; 2 pgs.

National Center for Biotechnology Information, National Library of Medicine, National Institutes of Health, GenBank Locus DR004312, Accession No. DR004312, "TC107600 Human placenta, large insert, pCMV expression library *Homo sapiens* cDNA clone TC107600 5' similar to *Homo sapiens* procollagen-lysine, 2 oxoglutarate 5-dioxygenase 2 (PLOD2), transcript varient 1, mRNA sequence", [online]. Bethesda, MD [retrieved on Sep. 8, 2005]. Retrieved from the Internet: <URL:http://www.ncbi.nlm.nih.gov/entrez/viewer.fcgi?db=nucleotide&val=6626 4185; 2 pgs.

National Center for Biotechnology Information, National Library of Medicine, National Institutes of Health, GenBank Locus NM 000935, Accession No. NM000935, "*Homo sapiens* procollagen-lysine, 2-oxoglutarate 5-dioxygenase 2 (PLOD2), transcript varient 2, mRNA", [online]. Bethesda, MD [retrieved on Sep. 8, 2005]. Retrieved from the Internet: <URL:http://www.ncbi.nlm.nih.gov/entrez/viewer.fcgi?db=nucleotide&val=6273 9165; 6 pgs.

National Center for Biotechnology Information, National Library of Medicine, National Institutes of Health, GenBank Locus NM 011961, Accession No. NM 011961, "*Mus musculus* procallagen lysine, 2-oxoglutarate 5-dioxygenase 2 (Plod2), mRNA", [online]. Bethesda, MD [retrieved on Sep. 8, 2005]. Retrieved from the Internet: <URL:http://www.ncbi.nlm.nih.gov/entrez/viewer.fcgi?db=nucleotide&val=6755 107; 4 pgs.

National Center for Biotechnology Information, National Library of Medicine, National Institutes of Health, GenBank Locus NM 175869, Accession No. NM 175869 XM 236485, "*Rattus norvegicus* procollagen lysine, 2 oxoglutarate 5-dioxygenase 2 (Plod2), mRNA", [online]. Bethesda, MD [retrieved on Sep. 8, 2005]. Retrieved from the Internet: <URL:http://www.ncbi.nlm.nih.gov/entrez/viewer.fcgi?db=nucleotide&val=3134 3608: 3 pgs.

National Center for Biotechnology Information, National Library of Medicine, National Institutes of Health, GenBank Locus NM 182943, Accession No. NM 182943, "*Homo sapiens* procollagen-lysine, 2-oxoglutarate 5-dioxygenase 2 (PLOD2), transcript varient 1, mRNA", [online]. Bethesda, MD [retrieved on Sep. 8, 2005]. Retrieved from the Internet:<URL:http://www.ncbi.nlm.nih.gov/entrez/viewer.fcgi?db=nucleotide&val=62739164; 6 pgs.

National Center for Biotechnology Information, National Library of Medicine, National Institutes of Health, GenBank Locus NT 005612, Accession No. NT 005612, "*Homo sapiens* chromosome 3 genomic contig", [online]. Bethesda, MD [retrieved on Sep. 8, 2005]. Retrieved from the Internet: <URL:http://www.ncbi.nlm.nih.gov/entrez/viewer.fcgi?db=nucleotide&val=3755 0867; 9 pgs.

National Center for Biotechnology Information, National Library of Medicine, National Institutes of Health, GenBank Locus NT 039476, Accession No. NT 039476, "*Mus musculus* chromosome 9 genomic contig, strain C57BL/6J", [online]. Bethesda, MD [retrieved on Sep. 8, 2005]. Retrieved from the Internet: <URL:http://www.ncbi.nlm.nih.gov/entrez/viewer.fcgi?db=nucleotide&val=6359 1790; 5 pgs.

National Center for Biotechnology Information, National Library of Medicine, National Institutes of Health, GenBank Locus NT 086641, Accession No. NT 086641, "*Homo sapiens* chromosome 3 genomic contig, alternate assembly", [online]. Bethesda, MD [retrieved on Sep. 8, 2005]. Retrieved from the Internet: <URL:http://www.ncbi.nlm.nih.gov/entrez/viewer.fcgi?db=nucleotide&val=5146 4125; 20 pgs.

National Center for Biotechnology Information, National Library of Medicine, National Institutes of Health, GenBank Locus HSU84573, Accession No. U84573, "*Homo sapiens* lysyl hydroxylase isoform 2 (PLOD2) mRNA, complete cds", [online]. Bethesda, MD [retrieved on Sep. 8, 2005]. Retrieved from the Internet: <URL:http://www.ncbi.nlm.nih.gov/entrez/viewerfcgi?db=nucleotide&val=2138 313; 3 pgs.

Nykanen et al., "ATP requirements and small interfering RNA structure in the RNA interference pathway", *Cell*, Nov. 2, 2001;107(3):309-321.

Parish et al., "The effect of minoxidil analogues and metabolites on the contraction of collagen lattices by human skin fibroblasts", *Br J Plast Surg*, 1995;48(3):154-160.

Parsonnet et al., "The effect of nonisodiametric design on the ease of extracting chronically implanted pacemaker leads", *Pacing Clin Electrophysiol*, Oct. 1997;20(10 Pt 1):2419-2421.

Pinnell et al., "Effects of minoxidil on cultured human skin fibroblasts", *Dermatologica*, 1987;175 Suppl 2:12-18.

Robins et al., "The chemistry of the collagen cross-links. Age-related changes in the reducible components of intact bovine collagen fibres", *Biochem J*, Apr. 1973;131(4):771-780.

Royce et al., "Failure of highly purified lysyl hydroxylase to hydroxylate lysyl residues in the non-helical regions of collagen", *Biochem J*, Sep. 1, 1985:230(2):475-480.

Sharp, "RNA interference—2001", *Genes Dev*, Mar. 1, 2001;15(5):485-490.

Uzawa et al., "Differential expression of human lysyl hydroxylase genes, lysine hydroxylation, and cross-linking of type 1 collagen during osteoblastic differentiation in vitro", *J Bone Miner Res*, Aug. 1999;14(8):1272-1280.

van der Slot et al., "Identification of PLOD2 as telopeptide lysyl hydroxylase, an important enzyme in fibrosis", *J Biol Chem*, Oct. 17, 2003;278(42):40967-40972.

van der Slot-Verhoeven, "Telopeptide lysyl hydroxylase: a novel player in the field of fibrosis", Thesis, Jun. 2005; 174 pgs.

Yamauchi et al., "Aging and cross-linking of skin collagen", *Biochem Biophys Res Commun*, Apr. 29, 1988;152(2):898-903.

Yamauchi et al., "The post-translational chemistry and molecular packing of mineralizing tendon collagens", *Connect Tissue Res*, 1993;29(2):81-98.

Yeowell et al., "Characterization of a partial cDNA for lysyl hydroxylase from human skin fibroblasts; lysyl hydroxylase mRNAs are regulated differently by minoxidil derivatives and hydralazine", *J Invest Dermatol*, Dec. 1992;99(6):864-869.

Brown et al., "RNA Interference in Mammalian Cell Culture: Design, Execution and Analysis of the siRNA Effect", *TechNotes* 2002;9(1):3-5.

Jarvis et al., "The siRNA Target Site Is an Important Parameter for Inducing RNAi in Human Cells", *TechNotes* 2001;8(5):3-5.

Yeowell et al., "Mutational analysis of the lysyl hydroxylase 1 gene (PLOD) in six unrelated patients with Ehlers-Danlos syndrome type VI: prenatal exclusion of this disorder in one family", *Hum Mutat*, Jul. 2000;16(1):1-9. Published online Jun. 23, 2000. [Retrieved on Oct. 18, 2005.] Retrieved from the internet: <URL:http://www3.interscience.wiley.com/cgi-bin/abstract/72508916/ABSTRACT.

Elbashir et al., "Analysis of gene function in somatic mammalian cells using small interfering RNAs," *Methods*, 2002; 26:119-213.

van der Slot et al., "Elevated formation of pyridinoline cross-links by profibrotic cytokines is associated with enhanced lysyl hydroxylase 2b levels," *Biochimica et Biophysica Acta*, 2005; 1741:95-102.

International Preliminary Report on Patentability and Written Opinion for PCT/US2005/025437; 13 pgs.

\* cited by examiner lysinonorleucine hydroxylysinonorleucine hydroxylysylpyrodinoline lysylpyrodinoline Relative GAPDH expression transfected fibroblasts Relative PLOD2 expression transfected fibroblast

SEQUENCE LISTING

```
<160> NUMBER OF SEQ ID NOS: 12

<210> SEQ ID NO 1
<211> LENGTH: 21
<212> TYPE: DNA
<213> ORGANISM: artificial
<220> FEATURE:
<223> OTHER INFORMATION: Small interfering RNA in which bases 1-19 are
      ribonucleic acids, and bases 20 and 21 are deoxynucleic acids.

<400> SEQUENCE: 1
gguccuuggu caaggagaat t                                               21

<210> SEQ ID NO 2
<211> LENGTH: 21
<212> TYPE: DNA
<213> ORGANISM: artificial
<220> FEATURE:
<223> OTHER INFORMATION: Small interfering RNA in which bases 1-19 are
      ribonucleic acids, and bases 20 and 21 are deoxynucleic acids.

<400> SEQUENCE: 2
uucuccuuga ccaaggacct t                                               21

<210> SEQ ID NO 3
<211> LENGTH: 21
<212> TYPE: DNA
<213> ORGANISM: artificial
<220> FEATURE:
<223> OTHER INFORMATION: Small interfering RNA in which bases 1-19 are
      ribonucleic acids, and bases 20 and 21 are deoxynucleic acids.

<400> SEQUENCE: 3
ggagaagaau ggagaggugt t                                               21

<210> SEQ ID NO 4
<211> LENGTH: 21
<212> TYPE: DNA
<213> ORGANISM: artificial
<220> FEATURE:
<223> OTHER INFORMATION: Small interfering RNA in which bases 1-19 are
      ribonucleic acids, and bases 20 and 21 are deoxynucleic acids.

<400> SEQUENCE: 4
caccucucca uucuucucct t                                               21

<210> SEQ ID NO 5
<211> LENGTH: 21
<212> TYPE: DNA
<213> ORGANISM: artificial
<220> FEATURE:
<223> OTHER INFORMATION: Small interfering RNA in which bases 1-19 are
      ribonucleic acids, and bases 20 and 21 are deoxynucleic acids.

<400> SEQUENCE: 5
gguacaauug cucuauugat t                                               21

<210> SEQ ID NO 6
<211> LENGTH: 21
```

```
<212> TYPE: DNA
<213> ORGANISM: artificial
<220> FEATURE:
<223> OTHER INFORMATION: Small interfering RNA in which bases 1-19 are
      ribonucleic acids, and bases 20 and 21 are deoxynucleic acids.

<400> SEQUENCE: 6
ucaauagagc aauuguacct t                                              21

<210> SEQ ID NO 7
<211> LENGTH: 21
<212> TYPE: DNA
<213> ORGANISM: artificial
<220> FEATURE:
<223> OTHER INFORMATION: Small interfering RNA in which bases 1-19 are
      ribonucleic acids, and bases 20 and 21 are deoxynucleic acids.

<400> SEQUENCE: 7
gcagauaagu uauuagucat t                                              21

<210> SEQ ID NO 8
<211> LENGTH: 21
<212> TYPE: DNA
<213> ORGANISM: artificial
<220> FEATURE:
<223> OTHER INFORMATION: Small interfering RNA in which bases 1-19 are
      ribonucleic acids, and bases 20 and 21 are deoxynucleic acids.

<400> SEQUENCE: 8
ugacuaauaa cuuaucugct g                                              21

<210> SEQ ID NO 9
<211> LENGTH: 21
<212> TYPE: DNA
<213> ORGANISM: artificial
<220> FEATURE:
<223> OTHER INFORMATION: Small interfering RNA in which bases 1-19 are
      ribonucleic acids, and bases 20 and 21 are deoxynucleic acids.

<400> SEQUENCE: 9
gaaaacgaug gauuccacat t                                              21

<210> SEQ ID NO 10
<211> LENGTH: 21
<212> TYPE: DNA
<213> ORGANISM: artificial
<220> FEATURE:
<223> OTHER INFORMATION: Small interfering RNA in which bases 1-19 are
      ribonucleic acids, and bases 20 and 21 are deoxynucleic acids.

<400> SEQUENCE: 10
uguggaaucc aucguuuuct t                                              21

<210> SEQ ID NO 11
<211> LENGTH: 21
<212> TYPE: DNA
<213> ORGANISM: artificial
<220> FEATURE:
<223> OTHER INFORMATION: Small interfering RNA in which bases 1-19 are
      ribonucleic acids, and bases 20 and 21 are deoxynucleic acids.

<400> SEQUENCE: 11
gauuuaugaa uucagccaat t                                              21

<210> SEQ ID NO 12
<211> LENGTH: 21
<212> TYPE: DNA
```

-continued

```
<213> ORGANISM: artificial
<220> FEATURE:
<223> OTHER INFORMATION: Small interfering RNA in which bases 1-19 are
      ribonucleic acids, and bases 20 and 21 are deoxynucleic acids.

<400> SEQUENCE: 12
uuggcugaau ucauaaauct g                                              21
```

MEDICAL DEVICES AND METHODS FOR REDUCING LOCALIZED FIBROSIS

CROSS-REFERENCE TO RELATED APPLICATIONS

The present application claims the benefit of U.S. Provisional Application No. 60/589,700, filed on 21 Jul. 2004, which is incorporated herein by reference in its entirety.

BACKGROUND

Implantation of biomedical devices leads to the formation of a poorly vascularized fibrous capsule that can lead to implant failure. Upon implantation, host neutrophils, macrophages, and lymphocytes migrate to the device surface and release cytokines and other proteins. Release of these molecules facilitates a cascade of processes that results in collagen production by local cells and the formation of a fibrous capsule around the material, walling it off from surrounding tissue. This process is also known as the foreign body response and develops in response to almost all implanted materials. Although a wide variety of possible therapeutic modalities have been suggested and consequently been investigated, for now there is no effective treatment available Thus, it remains desirable to find suitable other methods that reduce and even prevent said fibrotic entrapment.

SUMMARY

The present invention is directed to medical devices and the use thereof. The medical devices of the present invention include a substrate having associated therewith an active agent that suppresses the production and/or activity of a telopeptide lysyl hydroxylase (TLH) enzyme (preferably, human TLH enzyme) in collagen-producing cells in a subject. Such medical devices can be used in methods of the present invention that involve reducing, and preferably eliminating, aberrant crosslinking of collagen (and the consequent formation of fibrotic tissue), that being the consequence of TLH enzyme activity. Such crosslinking typically occurs at the site of contact between a medical device and tissue of the subject.

Thus, the present invention provides an active agent that suppresses the production and/or activity of a TLH enzyme to tissue at the immediate interface of the tissue and the medical device (which may or may not be the source of the active agent).

In one embodiment of the invention, there is provided a medical device that includes a substrate and an active agent associated with the substrate, wherein the active agent suppresses the production and/or activity of a TLH enzyme in collagen-producing cells. The active agent is "associated with the substrate" in a manner that allows localized delivery of the active agent directly to the interface of the medical device and the surrounding tissue.

The present invention also provides a method for delivering an active agent to a subject, the method involves: providing a medical device that includes a substrate and an active agent that suppresses the production and/or activity of a TLH enzyme in collagen-producing cells associated with the substrate; and placing the medical device in the subject in contact with collagen-producing cells.

Thus, in certain methods of the present invention a composition that includes an active agent can be delivered to the site of a medical device using the medical device per se (wherein the active agent is associated with the medical device). Alternatively, an active agent can be delivered to the site of a medical device using a variety of other methods. However, the active agent is delivered in a manner such that the active agent comes in contact with collagen-producing cells that are in contact with the medical device within a localized tissue region. That is, the active agent is delivered to the interface of the medical device and the surrounding tissue.

In one embodiment, the present invention provides a method of reducing fibrotic tissue formation at the site of a medical device in a subject. The method includes delivering to a localized tissue region at the site of the medical device an active agent that suppresses the production and/or activity of a TLH enzyme in collagen-producing cells. The medical device can deliver the active agent or the active agent can be delivered to the site using an alternate device (e.g., sponge, film, sheet, patch, or cuff, and pump, catheter) or composition. Herein, delivering to the site of the medical device means delivering the active agent to the interface of the medical device and the surrounding tissue.

In one embodiment, there is provided a medical device embedded in a matrix that includes the active agent, wherein the active agent suppresses the production and/or activity of a TLH enzyme in collagen-producing cells. In certain embodiments, the matrix that includes the active agent is a polynucleotide delivery matrix. In certain embodiments, the polynucleotide delivery matrix includes DNA encoding antisense, ribozyme, siRNA molecules that interfere with a PLOD2 gene (preferably, human PLOD2 gene) and inhibit the translation of a TLH enzyme or a gene encoding a protein involved in the production or processing of a TLH enzyme.

The phrase "active agent suppresses the production and/or activity of TLH enzyme" refers to a substance (e.g., small organic compound, DNA, RNA, etc.) that prevents or otherwise reduces the production of a TLH enzyme, or that prevents or otherwise reduces the activity of a TLH enzyme, or both affects the production and activity of a TLH enzyme. This can occur by directly targeting a TLH enzyme or a PLOD2 gene encoding a TLH enzyme, or a protein or gene involved in the production or processing of a TLH enzyme.

Herein, when reference is made to a PLOD2 gene or a TLH enzyme, reference is typically being made to the sequences of the human gene and enzyme, but the sequences of PLOD2 genes and TLH enzymes of other species are included where appropriate. Such sequences are disclosed in the NCBI database on the World Wide Web at ncbi.nlm.nig.gov and specifically at ncbi.nlm.nih.gov/entrez/query.fcgi?CMD=Display&DB=nucleotide.

The phrase "active agent associated with the substrate" means that one or more active agents are mixed within, bonded to, coated on, or otherwise intimately associated with a substrate that forms part of the medical device. The means by which the active agent is associated with the medical device is not limiting as long as the active agent is allowed to elute and be exposed to collagen-producing cells, thus providing for a reduction or prevention of aberrant crosslinking of the collagen.

By "subject" is meant an organism to which the active agent of the invention can be administered. Preferably, a subject is a mammal or mammalian cells, e.g., such as humans, cows, sheep, apes, monkeys, swine, dogs, cats, and the like. More preferably, a subject is a human.

As used herein "cell" is used in its usual biological sense, and does not refer to an entire multicellular organism. The cell may be present in an organism which may be a human but is preferably of mammalian origin, e.g., such as humans, cows, sheep, apes, monkeys, swine, dogs, cats, and the like. However, several steps of producing small interfering RNA, antisense, or ribozyme molecules may require use of prokaryotic cells (e.g., bacterial cell) or eukaryotic cell (e.g., mammalian cell) and thereby are also included within the term "cell."

By "complementary" it is meant that a molecule including one or more polynucleotides (DNA or RNA) can form hydrogen bond(s) (i.e., hybridize and form a duplex) with another molecule including one or more polynucleotides by either traditional Watson-Crick pairing or other non-traditional types. It will be understood that a complementary nucleotide sequence includes, in addition to a fully complementary nucleotide sequence, a substantially complementary nucleotide sequence that contains deletions or additions of one or more bases relative to the reference sequence, provided the complementary nucleotide sequence still retains the ability to hybridize with the reference nucleotide sequence.

The term "expression" defines the process by which a gene is transcribed into RNA (transcription); the RNA may be further processed into the mature small interfering RNA, antisense, or ribozyme molecules.

The terminology "expression vector" defines a vector or vehicle designed to enable the expression of an inserted sequence following transformation into a host. The cloned gene (inserted sequence) is usually placed under the control of control element sequences such as promoter sequences. The placing of a cloned gene under such control sequences is often referred to as being operably linked to control elements or sequences.

By the term "inhibit" or "inhibitory" it is meant that the activity of the target genes or level of mRNAs or equivalent RNAs encoding target genes is reduced below that observed in the absence of the provided small interfering RNA, ribozyme, or antisense molecules. Preferably the inhibition is at least 10% less, 25% less, 50% less, or 75% less, 85% less, or 95% less than in the absence of the small interfering RNA, ribozyme, or antisense molecules.

By "polynucleotide" as used herein is meant a molecule having nucleotides of any length, either ribonucleotides or deoxynucleotides. The term is often used interchangeably with nucleic acid or nucleic acid molecule. The polynucleotide can be single, double, or multiple stranded and may include modified or unmodified nucleotides or non-nucleotides or various mixtures and combinations thereof. It can include DNA or RNA. An example of a polynucleotide according to the invention is a gene that encodes for a small interfering RNA, even though it does not necessarily have its more common meaning for encoding for the production of protein.

By "RNA" is meant ribonucleic acid, a molecule consisting of ribonucleotides connected via a phosphate-ribose (sugar) backbone. By "ribonucleotide" is meant guanine, cytosine, uracil, or adenine or a nucleotide with a hydroxyl group at the 2' position of a beta-D-ribo-furanose moiety. As is well known in the art, the genetic code uses thymidine as a base in DNA sequences and uracil in RNA. One skilled in the art knows how to replace thymidine with uracil in a written polynucleotide to convert a written DNA sequence into a written RNA sequence, or vice versa.

By "small interfering RNA" is meant a polynucleotide which has complementarity in a substrate binding region to a specified gene target, and which acts to specifically guide enzymes in the host cell to cleave the target RNA. That is, the small interfering RNA by virtue of the specificity of its sequence and its homology to the RNA target, is able to cause cleavage of the RNA strand and thereby inactivate a target RNA molecule because it is no longer able to be transcribed. These complementary regions allow sufficient hybridization of the small interfering RNA to the target RNA and thus permit cleavage. One hundred percent complementarity often is necessary for biological activity and therefore is preferred, but complementarity as low as 90% may also be useful in this invention. The specific small interfering RNAs described in the present application are not meant to be limiting and those skilled in the art will recognize that all that is important in a small interfering RNA is that it have a specific substrate binding site which is complementary to one or more of the target nucleic acid regions.

Small interfering RNAs are double stranded RNA agents that have complementarity to (i.e., able to base-pair with) a portion of the target RNA (generally messenger RNA). Generally, such complementarity is 100%, but can be less if desired, such as at least 91%, at least 92%, at least 93%, at least 94%, at least 95%, at least 96%, at least 97%, at least 98%, or at least 99%. For example, 19 bases out of 21 bases may be base-paired. In some instances, where selection between various allelic variants is desired, 100% complementary to the target gene is required in order to effectively discern the target sequence from the other allelic sequence. When selecting between allelic targets, choice of length is also an important factor because it is the other factor involved in the percent complementary and the ability to differentiate between allelic differences.

The small interfering RNA sequence needs to be of sufficient length to bring the small interfering RNA and target RNA together through complementary base-pairing interactions. The small interfering RNA of the invention may be of varying lengths. The length of the small interfering RNA is preferably greater than or equal to ten nucleotides and of sufficient length to stably interact with the target RNA; specifically 15-30 nucleotides; more specifically, any integer between 15 and 30 nucleotides, such as 15, 16, 17, 18, 19, 20, 21, 22, 23, 24, 25, 26, 27, 28, 29, and 30. By "sufficient length" is meant a polynucleotide of greater than or equal to 15 nucleotides that is of a length great enough to provide the intended function under the expected condition. By "stably interact" is meant interaction of the small interfering RNA with a target polynucleotide (e.g., by forming hydrogen bonds with complementary nucleotides in the target under physiological conditions).

The terms "comprises" and variations thereof do not have a limiting meaning where these terms appear in the description and claims.

As used herein, "a," "an," "the," "at least one," and "one or more" are used interchangeably. Thus, for example, a composition that comprises "an" active agent can be interpreted to mean that the composition includes "one or more" active agent. Similarly, a medical device comprising "a" substrate can be interpreted to mean that the composition includes "one or more" substrates. Furthermore, a "composition" as used herein can consist of just one active agent without any other components (e.g., pharmaceutically acceptable carrier).

Also herein, the recitations of numerical ranges by endpoints include all numbers subsumed within that range (e.g., 1 to 5 includes 1, 1.5, 2, 2.75, 3, 3.80, 4, 5, etc.).

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

DETAILED DESCRIPTION OF ILLUSTRATIVE EMBODIMENTS

Figure 1:
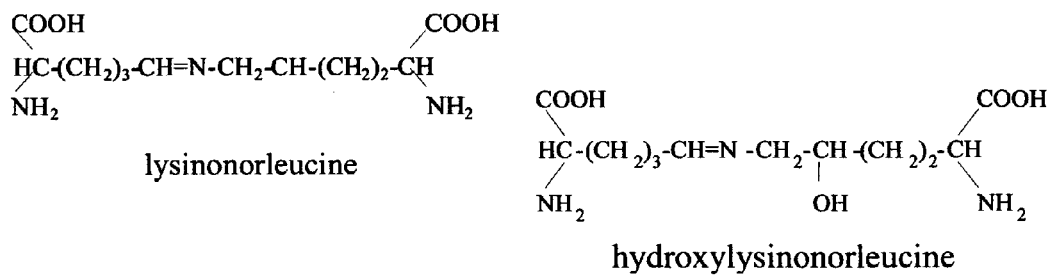
FIG. 1. Collagen crosslinked through the allysine route gives (hydroxy)lysinonorleucine crosslinks, and is typically found in type I collagen in skin, cornea, and certain tendons.

The present invention is directed to medical devices and the use thereof. The medical devices of the present invention include a substrate having associated therewith an active agent that suppresses the production and/or activity of a TLH enzyme (preferably, human TLH) in collagen-producing cells of a subject (preferably, a human). One or more active agents can be "associated with" a substrate by a number of means. For example, an active agent can be incorporated in a polymeric substrate and coated on a medical device, or an active agent can be incorporated into the matrix forming the body of the medical device, or an active agent can be bonded to a substrate that forms a part of the medical device. Thus, the means by which an active agent is associated with a medical device can range from coatings, pouches, patches, sponges, etc., that form a part of the medical device.

The means by which the active agent is associated with the medical device is not limiting as long as the active agent is allowed to elute and be exposed to collagen-producing cells, thus providing for a reduction or prevention of aberrant crosslinking of the collagen. Such contact can occur immediately upon the medical device contacting the collagen-producing cells or at some later time (e.g., after an initial lag time, the active agent can be eluted from the device). A wide variety of such means association of the medical device and the active agent are well known to, and can be readily implemented by, one of skill in the art.

In certain embodiments, the medical device may or may not have an active agent associated therewith. For example, in certain alternative embodiments, the active agent may not be directly a part of the medical device. In such embodiments, a composition that includes an active agent can be delivered to the site of the medical device (i.e., the localized tissue region in which the medical device is located) such that the active agent comes in contact with collagen-producing cells that are in contact with the medical device within the localized tissue region. Thus, the active agent is delivered to the interface of the medical device and the surrounding tissue, either directly or indirectly.

In collagen, crosslinking is initiated only after specific Lysine (Lys) or Hydroxylysine (Hyl) residues of the telopeptides are converted extracellularly by lysyl oxidase into the aldehydes allysine and hydroxyallysine, respectively. These aldehydes subsequently react with Lys, Hyl, or hystidyl residues of the triple helix.

There are two pathways of formation of crosslinks, depending on whether the residue in the telopeptide is a Lys (allysine route) or a Hyl (hydroxyallysine route). The aldehydes react with specific Lys or Hyl residues in the triple helical domain on juxtaposed neighboring molecules to form difunctional intermediates that mature into trifunctional crosslinks. The two pathways lead to different types of crosslinks. Only the difunctional crosslinks that result from the hydroxyallysine route are able to mature into the trifunctional crosslinks HP and LP.

It has recently been discovered that aberrant crosslinking of collagen, i.e., an increase of hydroxyallysine-derived crosslinks at the expense of allysine-derived crosslinks is a causative mechanism in the formation of fibrotic tissue, such as is seen in abnormal wound healing of the skin, such as in hypertrophic scarring, which contains large amounts of hydroxyallysine-derived crosslinks.

A predominance of these types of crosslinks is also found in collagen produced after wounding of the corneal stroma; the resulting scar shows markedly increased levels of hydroxyallysine derived crosslinks at the expense of allysine crosslinks. The studies on elevated hydroxyallysine-derived crosslinks in abnormal scarring have been confirmed, followed by reports on increased hydroxyallysine-derived crosslinks in other (mainly fibrotic) disorders, such as various lung diseases (respiratory distress syndrome, idiopathic pulmonary fibrosis, hypersensitivity pneumonitis, respiratory bronchiolitis, silicosis and bleomycin-induced lung fibrosis), chronic adriamycin nephropathy (an experimental model resulting in non-immunologic glomerulosclerosis and interstitial fibrosis), infarct scar of the myocardium, joint contractures, vessel luminal narrowing, lipodermatosclerosis, annulo-aortic ectasia, fibrotic lesions of Dupuytren's disease, skin of patients with lipoid proteinosis, diabetes, skin fibrosis due to chromoblastomycosis infection, skeletal muscle injury, tendon hypertrophy and various liver diseases such as in alveolar echinococcosis (a dense and irreversible fibrosis), hepatocellular carcinoma, alcoholic cirrhosis or cirrhotic livers induced by viral hepatitis or by *Schistosoma mansoni*. This aberrant crosslinking of collagen and the mechanism involving TLH enzyme and PLOD2 gene is described in U.S. Pat. Pub. 2003/0219852 (Bank et al.).

Collagen crosslinked through the hydroxyallysine route is more difficult to degrade than collagen crosslinked through the allysine route because the hydroxyallysine-based crosslinks are less susceptible to proteolytic degradation than collagen crosslinked by allysine-based residues. Thus, the production of collagen containing telopeptide lysine instead of telopeptide hydroxylysine, or alternatively the inhibition of telopeptide lysyl hydroxylase as to enhance the formation of allysine crosslinks at the expense of hydroxyallysine crosslinks, is an object of the present invention at the site of a medical device in a subject to reduce the formation of fibrotic tissue encapsulation of the medical device.

Bank et al. in U.S. Pat. Pub. 2003/0219852 concluded that one of the characteristics of fibrotic lesions is an upregulation of telopeptide lysyl hydroxylase (TLH). It has also been shown that PLOD2, the gene that encodes telopeptide lysyl hydroxylase, is highly expressed in cells associated with a variety of fibrotic disorders. The sequences of PLOD2 genes from various species are disclosed in the NCBI database on the World Wide Web at ncbi.nlm.nig.gov.

However, whereas Bank et al. described the mechanism of upregulation of PLOD2 and TLH being operant in a series of mainly fibrotic disorders, they did not do so for fibrous encapsulation associated with implanted medical devices. While the wound healing response associated with the implantation of medical devices, also called the foreign body response (FBR), shares many characteristics with normal wound healing or, for that matter, the healing response associated with one or more of the fibrotic disorders mentioned by Bank et al., it also has various distinguishing aspects.

The implantation procedure initiates a response to injury and mechanisms are activated to produce healing. The size, shape, and chemical and physical properties of the implanted material are responsible for variations in the intensity and time duration of the inflammatory and wound healing processes (see, e.g., Anderson, *Cardiovasc. Pathol.*, 2:33S-41S, (1993)). Local and systemic factors may play a role in the wound healing response to implanted materials. Local factors include the site (tissue or organ) of implantation, the adequacy of blood supply, and the potential for infection. Systemic factors may include nutrition, hematologic and immunologic derangements, glucocortical steroids, and pre-existing diseases such as atherosclerosis, diabetes, and infection.

The strong outcome that the size, shape, and chemical and physical properties of the implanted material can have on the eventual outcome of a healing response can be best exemplified by the classic paper published by S. D. Elek and P. E. Conen in 1957 (Elek et al., *Br. J. Exp. Pathol.*, 38:573-586, (1957)), which demonstrated strong enhancement of *staphylococcal* infections by silk sutures in a stitch abscess model. Whereas 1 million *S. aureus* microorganisms injected subcutaneously in the absence of the silk suture would not produce infection, an initial bacterial inoculum as small as 100 organisms could be sufficient to yield the formation of a large abscess in the presence of a suture. While focusing on infection, this classic paper gives a dramatic expose of how the presence of an implanted material can affect the local microenvironment triggering bodily responses that significantly differ from those in the absence of an implanted material.

Thus, it cannot be consequentially assumed that the mechanisms of the occurrence of fibrosis associated with, for example, liver cirrhosis, skin fibrosis, kidney fibrosis, would also be operant with the occurrence of device-associated fibrosis.

Overall, the mechanisms underlying biomaterial-mediated inflammatory responses (e.g., device-associated fibrosis) remain largely unknown. It is generally accepted that the most proximate trigger of inflammatory responses to device implants is the instantaneous deposition of proteins. The nature of the deposited protein layers is much dependent on the chemical and physical properties of the material surfaces. The adsorbed proteins trigger the attraction of phagocytic cells, and the nature of the deposited protein layers determines the types and concentrations of cytokines that are released by said phagocytes. The composition of released cytokines determines the eventual outcome of the biomaterial-associated inflammatory response and the extent to which a medical device is associated with adverse responses such as chronic inflammation (comprising the so-called foreign body giant cells—the primary distinguishing FBR hallmark) or fibrous encapsulation.

So, whereas the device-associated tissue response does share in a general sense the typical stages of normal wound healing, the underlying control mechanisms, i.e., the type and amount of pro- and anti-inflammatory cytokines that are released in the wound bed, can be and likely are quite different.

Surprisingly, however, the results presented herein indicate that the use of an active agent that suppresses the production and/or activity of a TLH enzyme in collagen-producing cells can be effective in preventing and/or reducing the formation of fibrosis at the interface of a medical device and the surrounding tissue.

Thus, effectuating that the collagen-producing cells at the interface of the medical device produce collagen containing telopeptide lysine instead of telopeptide hydroxylysine, or to inhibit production and/or activity of telopeptide lysyl hydroxylase and enhance the formation of allysine-derived crosslinks at the expense of hydroxyallysine-derived crosslinks, is an object of the present invention. This results in reducing or preventing the formation of fibrotic tissue encapsulating the medical device. This can be accomplished through the use of TLH inhibitors and/or PLOD2 inhibitors.

Thus, a preferred embodiment of the present invention provides a method of reducing or preventing fibrotic tissue formation at the site of a medical device in a subject (i.e., fibrotic encapsulation of an implanted medical device). The method includes delivering to a localized tissue region at the site of the medical device an active agent that suppresses the production of TLH enzyme in collagen-producing cells. The medical device can deliver the active agent or the active agent can be delivered to the site using an alternate device (e.g., sponge, film, sheet, patch, or cuff, and pump, catheter) or composition. Herein, delivering to the site of the medical device means delivering to the interface of the medical device and the surrounding tissue.

Active Agents

The active agent that suppresses the production and/or activity of TLH enzyme (preferably, human TLH enzyme) in collagen-producing cells can be a TLH inhibitor, a PLOD2 inhibitor, or both. That is, the active agent can function by inhibiting the production and/or activity of a TLH enzyme through a variety of mechanisms, such as by blocking its active site, for example. This can include inhibiting the production and/or activity of a protein that is involved in the production or processing of a TLH enzyme. Alternatively, the active agent can function by inhibiting the activity of a PLOD2 gene through a variety of mechanisms, such as those that occur in a variety of "gene silencing" technologies, including antisense, RNA interference, and ribozyme technologies. This can include inhibiting the activity of a gene that encodes a protein that is involved in the production or processing of a TLH enzyme.

The active agent can be a small organic molecule, as opposed to large biologic proteins, peptides, proteoglycans, glycosaminoglycans, and the like. Suitable small organic molecules will typically have a molecular weight under 1000 Daltons, preferably under 500 Daltons. Examples of such compounds include, but are not limited to, minoxidil and mimics thereof (i.e., compounds that function in the same or a similar manner to that of minoxidil), including its analogs (see, e.g., Murad et al., *Arch. Biochem. Biophys.*, 308(1):42-7, (1994)) and metabolites (e.g., minoxidil sulphate; see, Parish et al., *Br. J. Plast. Surg.*, 48(3):154-60, (1995)).

Alternatively, the active agent can be a large biologic protein, peptide, proteoglycan, glycosaminoglycan, and the like. Examples of such compounds include, but are not limited to heparan sulphate and its mimics (see, e.g., Alexakis et al., *FASEB J., May* 7, 2004).

A further alternative embodiment includes the use of polynucleotides as the "active agent" as used in "gene silencing" technologies, including antisense, RNA interference, and ribozyme technologies. Of these RNA interference is a preferred technology, which can be used to suppress the expression of a PLOD2 gene by destruction of the mRNA. RNA interference involves the use of small double stranded RNA molecules termed siRNA, which complex with endonucleases to cleave a specific mRNA target.

Small Interfering RNA (siRNA)

Small interfering RNA (or siRNA) described herein, is a segment of double stranded RNA that is from 15 to 30 nucleotides in length. It is used to trigger a cellular reaction known as RNA interference. In RNA interference, double-stranded RNA is digested by an intracellular enzyme known as Dicer, producing siRNA duplexes. The siRNA duplexes bind to another intracellular enzyme complex, which is thereby activated to target whatever mRNA molecules are homologous (or complementary) to the siRNA sequence. The activated enzyme complex cleaves the targeted mRNA, destroying it and preventing it from being used to direct the synthesis of its corresponding protein product. Recent evidence suggests that RNA interference is an ancient, innate mechanism for not only defense against viral infection (many viruses introduce foreign RNA into cells) but also gene regulation at very fundamental levels. RNA interference has been found to occur in plants, insects, lower animals, and mammals, and has been found to be dramatically more effective than other gene silencing technologies, such as antisense or ribozyme technologies.

Used as a biotechnology technique, siRNA methodology involves introducing into cells (or causing cells to produce) short, double-stranded molecules of RNA similar to those that would be produced by the Dicer enzyme from an invading double-stranded RNA virus. The artificially-triggered RNA interference process then continues from that point.

To deliver a small interfering RNA to a subject, a preferred method involves introducing DNA encoding for the siRNA, rather than the siRNA molecules themselves, into target cells. The DNA sequence encoding for the particular therapeutic siRNA can be specified upon knowing (a) the sequence for a small and accessible portion of the target mRNA (available in public human genome databases, particularly the NCBI database), and (b) well-known scientific rules for how to specify DNA that will result in production of a corresponding RNA sequence when the DNA is transcribed by cells. The DNA sequence, once specified, can be constructed in the laboratory from synthetic molecules ordered from a laboratory supplier, and inserted using standard molecular biology methods into one of several alternative vectors for delivery of DNA to cells. Once delivered into the target cells, those cells will themselves produce the RNA that becomes the therapeutic siRNA, by transcribing the inserted DNA into RNA. The result will be that the cells themselves produce the siRNA that will silence the targeted gene (e.g., PLOD2 gene or a gene that encodes a protein involved in the production or processing of a TLH enzyme). The result will be a reduction of the amount of the targeted protein (e.g., TLH enzyme or a protein involved in the production or processing of a TLH enzyme) produced by the cell.

In accordance with the present invention, small interfering RNA against specific mRNAs produced in the targeted cells prevents the production of a TLH enzyme. Thus, also within the scope of the present invention is the use of specifically tailored vectors designed to deliver small interfering RNA directly to targeted cells. The success of the designed small interfering RNA is predicated on their successful delivery to the targeted cells.

Small interfering RNA molecules have been shown to be capable of targeting specific mRNA molecules in human cells. Small interfering RNA vectors can be constructed to transfect human cells and produce small interfering RNA that cause the cleavage of the target RNA and thereby interrupt production of the encoded protein.

A small interfering RNA vector of the present invention will prevent production of the pathogenic protein by suppressing production of a TLH enzyme itself or by suppressing production of a protein involved in the production or processing of a TLH enzyme. Repeated administration of the therapeutic agent to the subject may be required to accomplish the desired goal.

Exemplary siRNA sequences include those disclosed in the Example Section.

In the present invention, the small interfering RNA are targeted to complementary sequences in the mRNA sequence coding for the production of the target protein (e.g., TLH enzyme or a protein involved in the production or processing of a TLH enzyme), either within the actual protein coding sequence, or in the 5' untranslated region or the 3' untranslated region. After hybridization, the host enzymes guided by the siRNA are capable of cleavage of the mRNA sequence. Perfect or a very high degree of complementarity is typically needed for the small interfering RNA to be effective. A percent complementarity indicates the percentage of contiguous residues in a polynucleotide that can form hydrogen bonds (e.g., Watson-Crick base pairing) with a second polynucleotide (e.g., 5, 6, 7, 8, 9, 10 out of 10 being 50%, 60%, 70%, 80%, 90%, and 100% complementary). "Perfectly complementary" means that all the contiguous residues of a polynucleotide will hydrogen bond with the same number of contiguous residues in a second polynucleotide. However, it should be noted that single mismatches, or base-substitutions, within the siRNA sequence can substantially reduce the gene silencing activity of a small interfering RNA.

In preferred embodiments of the present invention, a small interfering RNA is 15 to 30 nucleotides in length. In particular embodiments, the polynucleotide is 15, 16, 17, 18, 19, 20, 21, 22, 23, 24, 25, 26, 27, 28, 29, or 30 nucleotides in length. In preferred embodiments the length of the siRNA sequence can be between 19-30 base pairs, and more preferably between 21 and 25 base pairs, and more preferably between 21 and 23 base pairs.

In a preferred embodiment, the invention provides a method for producing a class of nucleic acid-based gene inhibiting agents that exhibit a high degree of specificity for the RNA of a desired target. SiRNAs can be constructed in vitro or in vivo using appropriate transcription enzymes or expression vectors.

Examples of vectors for delivery of foreign DNA to mammalian cells include those well known to one of skill in the art, such as plasmids or viral vectors, particularly adeno and adeno-associated viral sectors. Other well-known techniques could also be used including electroporation.

SiRNAs can be constructed in vitro using DNA oligonucleotides. These oligonucleotides can be constructed to include an 8 base sequence complementary to the 5' end of the T7 promoter primer included in the Silencer siRNA (Ambion Construction Kit 1620). Each gene specific oligonucleotide is annealed to a supplied T7 promoter primer, and a fill-in reaction with Klenow fragment generates a full-length DNA template for transcription into RNA. Two in vitro transcribed RNAs (one the antisense to the other) are generated by in vitro transcription reactions and then hybridized to each other to make double-stranded RNA. The double-stranded RNA product is treated with DNase (to remove the DNA transcription templates) and RNase (to polish the ends of the double-stranded RNA), and column purified to provide the siRNA that can be delivered and tested in cells.

Construction of siRNA vectors that express siRNAs within mammalian cells typically use an RNA polymerase III promoter to drive expression of a short hairpin RNA that mimics the structure of an siRNA. The insert that encodes this hairpin is designed to have two inverted repeats-separated by a short spacer sequence. One inverted repeat is complementary to the mRNA to which the siRNA is targeted. A string of six consecutive thymidines added to the 3' end serves as a pol III transcription termination site. Once inside the cell, the vector constitutively expresses the hairpin RNA. The hairpin RNA is processed into an siRNA that induces silencing of the expression of the target gene, which is called RNA interference (RNAi).

In most siRNA expression vectors described to date, one of three different RNA polymerase III (pol III) promoters is used to drive the expression of a small hairpin siRNA. These promoters include the well-characterized human and mouse U6 promoters and the human H1 promoter.

Antisense Molecules

In certain embodiments of the invention, antisense technology can be used to inhibit the function of polynucleotide molecules encoding a TLH enzyme and ultimately modulate the amount of TLH enzyme produced. Other techniques for inhibiting expression of a TLH enzyme can involve genetically or biochemically manipulating the bioactivity of regulatory elements, control sequences, factors, cofactors, and the like to inhibit the expression of gene encoding a TLH enzyme and/or a protein involved in the production or processing of a TLH enzyme.

Inhibition of the expression of a TLH enzyme can be accomplished by providing an antisense molecule. As used herein, an "antisense molecule" is a polynucleotide that specifically hybridizes with mRNA or DNA encoding a TLH enzyme. Such hybridization with mRNA interferes with the normal role of mRNA and causes a modulation of its function. The functions of mRNA to be interfered with include all vital functions such as, for example, translocation of the RNA to the site of protein translation, translation of protein from the RNA, splicing of the RNA to yield one or more mRNA species, and catalytic activity which may be engaged in by the RNA. The overall effect of such interference with mRNA function is modulation of the expression of TLH. In the context of this invention, "modulation" means either an increase (stimulation) or a decrease (inhibition) in the expression of a gene. In the context of the present invention, inhibition is the preferred form of modulation of gene expression.

An "antisense molecule" of the present invention contains at least one polynucleotide that is "antisense" or "sense" to at least a portion of an endogenous gene encoding a TLH enzyme. A polynucleotide that is "antisense to a gene" includes a nucleotide sequence that is complementary to at least a portion of the coding strand of the gene, or is complementary to at least a portion of a processed or unprocessed RNA transcript of that gene. In the case of an antisense polynucleotide that is complementary to at least a portion of the coding strand of the gene, the antisense nucleotide sequence may be operably linked to control sequences necessary to facilitate transcription of the sequence to yield an RNA transcript. It will be observed that an antisense polynucleotide that is complementary to a portion of the coding strand of a gene may also be complementary to a portion of the unprocessed RNA transcript of the gene. An unprocessed RNA transcript is often referred to as precursor RNA or "pre-RNA." Processed RNA transcripts include, for example, mRNA.

Similarly, a polynucleotide that is in a "sense" orientation with respect to a gene includes a nucleotide sequence that is complementary to at least a portion of the noncoding or "template" strand of the gene, or is complementary to at least a portion of a cDNA derived from a mRNA transcript of the gene. A transcription product of a "sense" nucleotide sequence supplied as a coding strand is essentially identical to all or a portion of a transcription product (either processed or unprocessed, depending on the selected nucleotide sequence) of an endogenous gene.

It will be understood by those skilled in the art that the present invention broadly includes antisense molecules that are capable of binding to the DNA or mRNA sense strand coding for a TLH enzyme or a protein involved in the production or processing of a TLH enzyme. It will also be understood that mRNA includes not only the ribonucleotide sequences encoding a protein, but also regions including the 5'-untranslated region, the 3'-untranslated region, the 5'-cap region and the intron/exon junction regions. The functions of DNA to be interfered with include replication and transcription. The functions of RNA to be interfered with include all vital functions such as, for example, translocation of the RNA to the site of protein translation, translation of protein from the RNA, splicing of the RNA to yield one or more mRNA species, and catalytic activity which may be engaged in or facilitated by the RNA. The overall effect of such interference with target polynucleotide function is a modulation of the expression of TLH.

An antisense molecule may be complementary to the open reading frame (ORF) or "coding region," which is known in the art to refer to the region between the translation initiation codon and the translation termination codon, is also a region which may be targeted effectively. Other target regions include the 5' untranslated region (5' UTR), known in the art to refer to the portion of an mRNA in the 5' direction from the translation initiation codon, and thus including nucleotides between the 5' cap site and the translation initiation codon of an mRNA or corresponding nucleotides on the gene, and the 3' untranslated region (3' UTR), known in the art to refer to the portion of an mRNA in the 3' direction from the translation termination codon, and thus including nucleotides between the translation termination codon and 3' end of an mRNA or corresponding nucleotides on the gene. The 5' cap of an mRNA comprises an N7-methylated guanosine residue joined to the 5'-most residue of the mRNA via a 5'-5' triphosphate linkage. The 5' cap region of an mRNA is considered to include the 5' cap structure itself as well as the first 50 nucleotides adjacent to the cap. The 5' cap region may also be a preferred target region for a complementary antisense molecule.

Although some eukaryotic mRNA transcripts are directly translated, many contain one or more regions, known as "introns," which are excised from a transcript before it is translated. The remaining (and therefore translated) regions are known as "exons" and are spliced together to form a continuous mRNA sequence. mRNA splice sites, i.e., intron-exon junctions, may also be preferred target regions, and are particularly useful in situations where aberrant splicing is implicated in disease, or where an overproduction of a particular mRNA splice product is implicated in disease. Aberrant fusion junctions due to rearrangements or deletions are also preferred targets. It has also been found that introns can also be effective, and therefore preferred, target regions for antisense compounds targeted, for example, to DNA or pre-mRNA.

In addition to hybridizing under standard conditions to one or more PLOD2 sequences, for example, the antisense molecules of the present invention also inhibit the expression of one or more TLH enzymes. The antisense molecules of the present invention are selected for the ability to inhibit the expression of one or more TLH enzymes or proteins involved in the production or processing of a TLH enzyme. Thus, the antisense molecules of the present invention may include selected portions of larger known sequences, such portions chosen for their ability to effectively inhibit TLH expression and/or activity.

The antisense molecules of the present invention may be from 100 to 3000 nucleotides in length. In addition to those antisense molecules that are 100 nucleotides in length, and those antisense molecules that are 3000 nucleotides in length, all intermediate size compounds are also contemplated to be useful in the practice of the present invention. Thus, for example, antisense molecules that are 2500 nucleotides in length, 2000 nucleotides in length, 1500 nucleotides in length, 1000 nucleotides in length, 900 nucleotides in length, 800 nucleotides in length, 700 nucleotides in length, 600 nucleotides in length, 500 nucleotides in length, 400 nucleotides in length, 300 nucleotides in length, and 200 nucleotides in length, are also contemplated to fall within the scope of the present disclosure.

Likewise, antisense molecules that are shorter than 100 nucleotides are also contemplated to fall within the scope of the present disclosure. Antisense molecules in accordance with this invention may include from 8 to 99 nucleotides. In addition to those antisense molecules that are 8 nucleotides in length, and those antisense molecules that are 99 nucleotides in length, all intermediate size compounds are also contemplated to be useful in the practice of the present invention. Thus, antisense molecules that are 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, and/or 99 nucleotides in length are also contemplated to fall within the scope of the present disclosure.

There is no obligate requirement that the antisense molecules be exactly 100% complementary to a given target sequence on a TLH mRNA. In fact, the only requirement is that the antisense molecules have sufficient homology to the gene or the mRNA encoding a TLH enzyme, for example, so that upon hybridizing to the complementary region, a reduction in either the transcription of the TLH gene and/or a reduction in the translation of TLH enzyme from the mRNA is observed.

Antisense molecules may also include such molecules as ribozymes, external guide sequence (EGS) oligonucleotides (oligozymes), and other short catalytic RNAs or catalytic oligonucleotides that hybridize to the target polynucleotide and modulate its expression.

The antisense molecules of the present invention include molecules of biological origin and genetic vector constructs designed to direct the in vivo synthesis of antisense molecules. The antisense molecules for use as described herein can also be synthesized in vitro by any method known to those of skill in this art. For example, the antisense molecules of the present invention may be made by the well-known technique of solid phase synthesis. Equipment for such synthesis is sold by several vendors, including, for example, Applied Biosystems (Foster City, Calif.). Any other means for such synthesis known in the art may additionally or alternatively be employed.

It is well known to use similar techniques to prepare oligonucleotides such as the phosphorothioates and alkylated derivatives. Antisense oligonucleotides are typically designed to resist degradation by endogenous nucleolytic enzymes by using such linkages as phosphorothioate, methylphosphonate, sulfone, sulfate, ketyl, phosphorodithioate, phosphoramidate, phosphate esters, and other such linkages as is known to one of skill in the art.

In other preferred oligonucleotide mimetics, both the sugar and the internucleoside linkage, i.e., the backbone, of the nucleotide units are replaced with novel groups. The base units are maintained for hybridization with an appropriate polynucleotide target compound. One such oligomeric compound, an oligonucleotide mimetic that has been shown to have excellent hybridization properties, is referred to as a peptide polynucleotide (PNA). In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone.

Chimeric antisense compounds of the invention may be formed as composite structures of two or more oligonucleotides, modified oligonucleotides, oligonucleosides and/or oligonucleotide mimetics as described above. Such compounds have also been referred to in the art as hybrids or gapmers.

Ribozymes

The active agents of the present invention also include ribozymes. A ribozyme is an RNA molecule that specifically cleaves RNA substrates, such as mRNA, resulting in inhibition or interference with cell growth or expression. There are at least five known classes of ribozymes involved in the cleavage and/or ligation of RNA chains. Ribozymes can be targeted to any RNA transcript and can catalytically cleave such transcript, as is known to one of skill in the art. The ribozymes of the present invention include an antisense nucleotide sequence, as described herein, for targeting the ribozyme to an RNA transcript encoding a TLH enzyme. Ribozymes may be delivered to the targeted cells by DNA encoding the ribozyme linked to a eukaryotic promoter, such as a eukaryotic viral promoter or a eukaryotic tissue specific promotor, such that upon introduction into the nucleus, the ribozyme will be directly transcribed. In such instances, the construct will also include a nuclear translocation sequence, generally as part of the ligand or as part of a linker between the ligand and polynucleotide binding domain.

Medical Devices and Delivery Compositions

The medical device can be an implantable device or an extracorporeal device. The devices can be of short-term temporary use or of long-term permanent implantation, which typically have associated therewith the formation of fibrotic tissue. In certain embodiments, suitable devices are those that are typically used to provide for medical therapy and/or diagnostics in heart rhythm disorders, heart failure, valve disease, vascular disease, diabetes, neurological diseases and disorders, orthopedics, neurosurgery, oncology, ophthalmology, and ENT surgery.

Suitable examples of medical devices include, but are not limited to, a stent, stent graft, anastomotic connector, synthetic patch, lead, electrode, needle, guide wire, catheter, sensor, surgical instrument, angioplasty balloon, wound drain, shunt, tubing, infusion sleeve, urethral insert, pellet, implant, blood oxygenator, pump, vascular graft, vascular access port, heart valve, annuloplasty ring, suture, surgical clip, surgical staple, pacemaker, implantable defibrillator, neurostimulator, orthopedic device, cerebrospinal fluid shunt, implantable drug pump, spinal cage, artificial disc, replacement device for nucleus pulposus, ear tube, and intraocular lens.

A medical device may be embedded within, or otherwise associated with, a delivery matrix. This delivery matrix can be any matrix material containing an active agent, including polynucleotide(s) encoding PLOD2 inhibitors and/or TLH inhibitors, for localized delivery. Systems such as this are described, for example, in U.S. Pat. No. 5,962,427 (Goldstein et al.), as well as in Kyriakides et al., *Molecular Therapy*, 2, 842 (2001), and Bonadio et al., *Nature Medicine*, 5, 753 (1999). The polynucleotides may be antisense or ribozyme or siRNA molecules that interfere with a PLOD2 gene, for example, and inhibit the translation of a TLH protein, or a protein involved in the production or processing of a TLH protein.

Alternatively, the polynucleotide may encode for an antisense, ribozyme, or siRNA molecule. Then interference with a PLOD2 gene, for example, and inhibition of the translation of a TLH enzyme, for example, is obtained when the polynucleotide is released from the delivery matrix and said polynucleotide is expressed in and the encoded antisense, ribozyme, or siRNA molecule is delivered by the cells and tissues surrounding said medical device.

The transferred DNA may be integrated into the genome of the target cell or not, as is possible with the use of this type of system.

In addition to embedding a medical device within a delivery matrix, the delivery matrix may be otherwise associated with the medical device, for example, as an adjunctive implant (e.g., sponge, rod, etc.), depot injection (e.g., polymer microspheres) or liquid formulation or emulsion injection (e.g., liposomes). In this case the active agent formulation is administered to the subject during implant of a device, but not attached to the device.

The material that forms a polynucleotide delivery matrix, a coating on a medical device, or otherwise forms a part of a medical device (e.g., pouches, patches, sponges, etc.), or that is included in compositions that deliver an active agent to the site of a medical device, is typically biocompatible. A material is generally "biocompatible" if it does not produce an adverse, allergic, or other undesired reaction when administered to a mammalian host. Such materials may be formed from both natural or synthetic materials.

Such materials may include, but are not limited to, biodegradable or non-biodegradable materials formulated into scaffolds that support cell attachment and growth, for example. Such materials may include synthetic polymers or naturally occurring proteins such as collagen, other extracellular matrix proteins, or other structural macromolecules. The material may be non-biodegradable in instances where it is desirable to leave permanent structures in the body; or biodegradable where the active agent is required only for a short duration of time.

In certain embodiments, such as for the polynucleotide delivery matrices, these materials may take the form of coatings, sponges, films, sheets, cuffs, implants, tubes, rods, microbeads, lyophilized components, gels, patches, powders, or nanoparticles. In addition, for certain embodiments, such as for the polynucleotide delivery matrices, the materials used in the delivery of active agents described herein can be designed to allow for sustained release (e.g., of the active agent) over prolonged periods of time.

Depending on the embodiment in which it is used, physical and chemical characteristics, such as, e.g., biocompatibility, biodegradability, strength, rigidity, interface properties and even cosmetic appearance may be considered in choosing such a material, as is well known to those of skill in the art. Numerous examples of useful polymers are well known to those of skill in the art. It is to be understood that virtually any polymer that is now known or that will be later developed suitable for the sustained or controlled release of active agents may be employed in the present invention.

For certain embodiments, examples of useful non-degradable polymers include silicones, polyurethanes, silicone-urethane copolymers, polyimides, polysulphones, polyaryls, polyetheretherketones, polyetherketoneketones, polyacrylates, polymethacrylates, polymethylmethacrylates, polybutylmethacrylates, polytetrafluoroethylene, polyesters, polyolefins, polyethylenes, polypropylenes, polyamides, polyvinylchlorides, and epoxides.

For certain embodiments in which a biodegradable material (e.g., one that is capable of being reabsorbed into the body) is desired, suitable materials include, for example, synthetic organic polymers such as polyesters, polyanhydrides, polyethers, poly(orthoesters), poly(ether-esters), polyphosphazenes, poly(amino acids), polypeptides, and polyesteramides. More specifically, suitable biodegradable polymers materials are polylactic acid, polyglycolide, polylactic polyglycolic acid copolymers ("PLGA"), polycaprolactone ("PCL"), poly(dioxanone), poly(trimethylene carbonate) copolymers, polyglyconate, poly(propylene fumarate), poly(ethylene terephthalate), poly(butylene terephthalate), polyethyleneglycol, polycaprolactone copolymers, polyhydroxybutyrate, polyhydroxyvalerate, tyrosine-derived polycarbonates and any random or (multi-) block copolymers, such as bipolymer, terpolymer, quaterpolymer, etc., that can be polymerized from the monomers related to afore-listed homo- and copolymers.

Another particular group of suitable materials encompass the natural polymers. This group includes, for example, polysaccharides, proteins and polypeptides, glycosaminoglycans, proteoglycans, collagen, elastin, hyaluronic acid, dermatan sulfate, chitin, chitosan, pectin, (modified) dextran, (modified) starch and modifications, mixtures or composites thereof.

A particularly suitable material is fibrous collagen, which may be lyophilized following extraction and partial purification from tissue and then sterilized. In addition, lattices made of collagen and glycosaminoglycan (GAG) may be used in the practice of the invention. At least 20 different forms of collagen have been identified and each of these collagens may be used in the practice of the invention. Recombinant collagen may also be employed, as may be obtained from a collagen-expressing recombinant host cell, including bacterial, yeast, mammalian, plant and insect cells. The collagen used in the invention may, if so desired and applicable, be supplemented with additional minerals, such as calcium, e.g., in the form of calcium phosphate. Both native and recombinant type collagen may be supplemented by admixing, absorbing, or otherwise associating with, additional minerals in this manner.

A preferred embodiment of the present invention includes a coating on the medical device, wherein the coating includes the active agent. Another preferred embodiment includes a medical device imbedded within a matrix, such as a sponge, or a sponge or other implantable material that provides for adjunctive therapy at the site of medical device implant.

Delivery

Whether it is a part of a medical device or delivered in a composition to be in contact with collagen-producing cells at the site of the medical device, the present invention may provide one or more active agents (e.g., a PLOD2 inhibitor, a TLH inhibitor, or both) to the desired localized tissue region with various active agent residence half-life times, generally of at least 24 hours. For example, the residence half-life of an active agent may be at least 1 day, at least 3 days, at least 1 week, at least 3 weeks, at least 4 weeks, at least 5 weeks, at least 6 weeks, or even longer.

An active agent composition can be designed to achieve constant or pulsed delivery to the localized tissue region at the site of the medical device. Pulsed delivery may be desirable in order to provide intermittent dosing of an active agent to the local tissue region over time. For example, a combination of biodegradable polymers can be used that have differing degradation rates, and thus active agent release rates. The composition may contain a homogeneous mixture of various biodegradable polymers, or the polymers may be utilized in a segmented fashion to achieve complex degradation profiles. The composition may also include various polymers to achieve zero-order, first-order, or other release. Also, the active agent release timing may either be regular, e.g., initially and once weekly for several weeks, or it may be irregular, e.g., initially and then 3 days, 2 weeks, and 2 months apart.

If the active agent is not a part of the medical device, a composition that includes one or more active agents may be delivered to the localized tissue region at the site of the medical device via any suitable route, e.g., including, but not limited to, a subcutaneous, intradermal, intramuscular, intrathecal, intra-organ, intratumoral, intralesional, intravesicle, and intraperitoneal route of delivery. A "localized tissue region" will generally be a relatively small portion of the body, e.g., less than 10% by volume, and often less than 1% by volume, where a medical device is located. This includes the interface of the medical device and the surrounding tissue.

For example, the localized tissue region will typically be on the order of no more than 500 cubic centimeters ($cm^3$), often less than 100 $cm^3$, and in many instances 10 $cm^3$ or less. For some applications the localized tissue region will be 1 $cm^3$ or less. However, in certain instances the localized tissue region may be a particularly large region, up to several liters. The compositions may be delivered using, e.g., needle injection, surgical, laparoscopic, or catheter implantation, microneedle array, high-velocity particle implantation, or any other known method for introducing a composition into a localized tissue region. The medical device itself could provide the means of delivery of a composition containing one or more active agents, even if the active agent is not a part of the medical device. Delivery to the localized tissue region may be in conjunction with image guiding techniques using, for example, ultrasound, MRI, real-time X-ray (fluoroscopy), etc.

The present invention also provides kits containing a medical device, an active agent, and other components for making the combination of the medical device and active agent. For example, in some instances the kits will contain preformed polynucleotide delivery matrices thereby allowing the physician to directly administer the matrix within the body at the site of the medical device. Alternatively, the kits may contain the components necessary for formation of a polynucleotide delivery matrix, for example. In such cases the physician may combine the components to form the polynucleotide delivery matrices, which may then be used therapeutically by placement within the body. In one embodiment of the invention, polynucleotide delivery matrices may be used to coat surgical devices such as suture materials or other medical devices such as implants. In another embodiment of the invention, a sponge may be provided in the kit, which may then be impregnated with the active agent by medical personnel prior to placement in the body.

EXAMPLES

Objects and advantages of this invention are further illustrated by the following examples, but the particular materials and amounts thereof recited in these examples, as well as other conditions and details, should not be construed to unduly limit this invention.

Example 1

Identification of Crosslinking in the Fibrocollagenous Tissue on Explanted Human Leads Ten explanted leads were retrieved and submitted for analysis. Six of these leads contained sufficient amounts of fibrous capsule tissue for analysis. Hydroxylysylpyrodinoline (HP) crosslinks were quantified in acid hydrolysates of unreduced tissue samples by RP-HPLC (Bank et al., *J. Chromatogr. B*, 703:37-44, (1997)). Above and beyond characterization of the determination of hydroxylysylpyridinoline (HP) crosslink levels, the fibrous capsule tissue on several explanted leads was also more fully characterized to include determination of lysylpyrodinoline (LP) crosslink levels, number of hydroxylysine residues per collagen molecule and the hydroxyproline:proline ratio. The latter is a measure for the ratio of collagenous to non-collagenous proteins in the fibrous tissue. For 100% fibrillar collagen the Hyp/Pro ratio is 0.81. In collagen crosslinking is initiated only after specific Lysine (Lys) or Hydroxylysine (Hyl) residues of the telopeptides are converted extracellularly by lysyl oxidase into the aldehydes allysine and hydroxyallysine, respectively. These aldehydes subsequently react with Lys, Hyl, or hystidyl residues of the triple helix.

Figure 2:
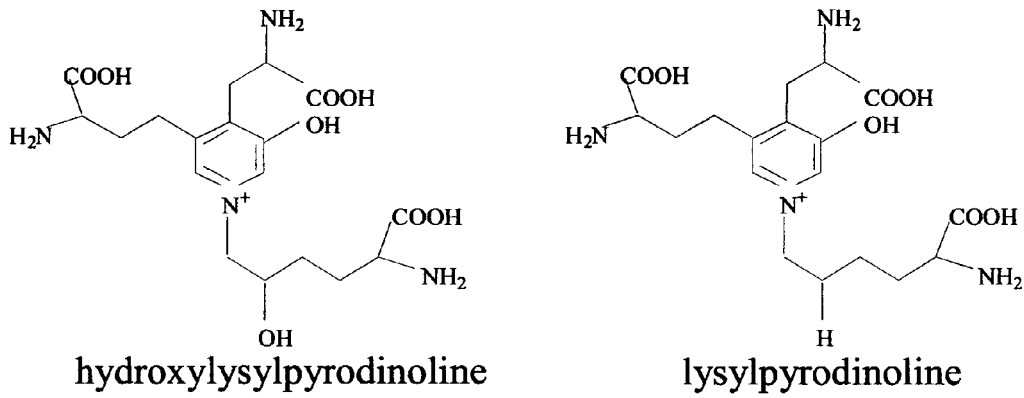
FIG. 2. Collagen crosslinked through the hydroxyallysine route gives (hydroxy)lysylpyrodinoline (HP and LP, respectively) crosslinks, and is typically found in type I collagen in bone and type II collagen in cartilage.

There are two pathways of formation of crosslinks, depending on whether the residue in the telopeptide is a Lys (allysine route) or a Hyl (hydroxyallysine route) (see FIG. 1 and FIG. 2). The aldehydes react with specific Lys or Hyl residues in the triple helical domain on juxtaposed neighboring molecules to form difunctional intermediates that mature into trifunctional crosslinks. The two pathways lead to different types of crosslinks. Only the difunctional crosslinks that result from the hydroxyallysine route are able to mature into the trifunctional crosslinks HP and LP.

As can be derived from Table 1 below, fibrous capsule tissue contained 1.7±0.9 HP crosslink/collagen molecule. The determined number of hydroxylysine residues per collagen molecule is well within the typical physiological range and does not provide any evidence for aberrant processing of collagen in the fibrous capsule tissue, nor for increased hydroxylation of triple-helical lysines.

TABLE 1

Results of characterization of fibrous capsule tissue associated with explanted leads.

| Lead ID | n HP crosslinks/ collagen molecule | n LP crosslinks/ collagen molecule | n Hyl residues/ collagen molecule | Hyp/Pro ratio |
|---|---|---|---|---|
| 1. | 1.1 | — | — | — |
| 2. | 0.8 | — | — | — |
| 3. | 1.2 | — | — | — |
| 4. | 2.6 | 0.2 | 24.4 | 0.57 |
| 5. | 3.1 | 0.4 | 23.6 | 0.59 |
| 6. | 1.3 | 0.2 | 17.1 | 0.57 |

As the results obtained demonstrated, the concentration of HP type crosslinks in the fibrous capsule associated with the explanted leads was very high when compared to typical tissue specific levels as listed in Table 2. This is undoubtedly indicative of a switch toward the telopeptide-hydroxylysyl-crosslink pathway, and associated upregulation of the telopeptide lysyl hydroxylase (TLH) enzyme.

TABLE 2

Overview of tissue specific level of HP crosslinks/collagen molecule.

| Tissue Type | HP crosslinks/collagen molecule |
|---|---|
| Skin | 0.03 |
| Tendon | 0.5-0.8 |
| Bone | 0.3 |

TABLE 2-continued

Overview of tissue specific level of HP crosslinks/collagen molecule.

| Tissue Type | HP crosslinks/collagen molecule |
|---|---|
| Cartilage | 1.6 |
| Aorta | 0.4 |
| Lung tissue | 0.3 |
| Muscle | 0.2 |

Example 2

Quantification of PLOD2 Expression in Human Fibroblasts

Fibroblasts play a central role in the development of fibrous encapsulation of implants by way of the fact that fibroblasts are the main producers of collagen. In designing an anti-fibrous encapsulation therapy wherein the active agent suppresses the production and/or activity of a TLH enzyme it is thus deemed of significant importance to demonstrate the active agent's activity and efficacy using fibroblast cells. In this experiment three different siRNA designs, targeting PLOD2, were tested using human fibroblasts. RNA isolated from transfected human fibroblasts was quantified using Real Time RT-PCR and compared with RNA isolated from non-transfected cells.

Materials & Methods:

```
siRNA #1:
sense sequence
5'GGUCCUUGGUCAAGGAGAAtt 3'      (SEQ ID NO:1)

anti-sense sequence
5'UUCUCCUUGACCAAGGACCtt 3'      (SEQ ID NO:2)

siRNA #2:
sense sequence
5'GGAGAAGAAUGGAGAGGUGtt 3'      (SEQ ID NO:3)

anti-sense sequence
5'CACCUCUCCAUUCUUCUCCtt 3'      (SEQ ID NO:4)

siRNA #3:
sense sequence
5'GGUACAAUGCUCUAUUGAtt 3'       (SEQ ID NO:5)

anti-sense sequence
5'UCAAUAGAGCAAUUGUACCtt 3'      (SEQ ID NO:6)
```

Cell culture: Human fibroblasts (CCD-1077Sk cells, ATCC) were cultured in Iscoves modified Dulbecco's medium supplemented with 10% fetal bovine serum, 1% PSN antibiotics, 1% Fungizone antimycotics (Gibco) at 37° C. and 5% $CO_2$.

Transfection: $2\times10^5$ fibroblasts were plated in a 25 square centimeter ($cm^2$) culture flask containing 7 milliliters (mL) of growth medium without antibiotics one day before transfection so that they will be 50% confluent at the time of transfection. The cells were transfected with 840 picomoles (pmol) siRNA (final concentration: 100 nanomolar (nM)) using 14 microliters (μL) Lipofectamine 2000 transfection reagent and 700 μL Opti-MEM I (Invitrogen). Growth medium was changed after 12 hours and RNA was isolated after 36 hours of incubation.

Semi-quantification: The cells were harvested from the culture flasks with 1 mL of Trypsin-EDTA (0.25% Trypsin, 1 millimolar (mM) EDTA•4Na, Gibco). Total RNA was isolated from the cells using the RNeasy mini kit (Qiagen) and gDNA was removed using an on column DNase treatment (30 minutes (min)). After isolation, absence of gDNA was confirmed by a PCR using the MCP-1 primerset. The A260 was measured to correct for the amount of RNA. Reverse transcription took place using the iscript cDNA synthesis kit (Bio-Rad). Subsequently, two Real Time PCR's were carried out using iQ SYBR Green supermix (Bio-Rad), one with PLOD2 primerset and one with the GAPDH primerset which is used as internal control. The GAPDH standard curve was generated by amplifying the following numbers of DNA control molecules (in triple) in a 25 µL reaction: $1\times10^{10}$, $1\times10^9$, $1\times10^8$ . . . to $1\times10^3$. The DNA control molecule was chemically synthesized (Life Technologies) and has the same sequence as the PCR products. The PLOD2 standard curve was made by amplifying the cDNA of an untransfected control sample undiluted, 10× diluted, 100× diluted and 1000× diluted. The undiluted sample was set at 100% expression the others at respectively 10%, 1%, and 0.1% expression.

The Real Time PCR's for LOX and COL1A2 were performed the same way as the Real Time PCR for PLOD2.

Results:

Gel electrophoresis: The quality of the RNA was checked by gel electrophoresis. High quality RNA has two bands, the 28S rRNA band and the 18S rRNA band. For high quality RNA the intensity of these bands should be 2:1; this was indeed confirmed.

Control PCR: To confirm absence of gDNA a real time PCR was carried out using SYBR Green. Besides the positive control, one sample crossed the threshold and gave a significant signal. Since this occurred very late in the reaction (cycle 38), it was neglected as non-significant.

Reverse Transcriptase Reaction: All RNA samples were diluted to the same concentration before continuing with the RT-reaction. The entire 40 µL of diluted sample (3 micrograms (µg) RNA) was reverse transcribed in a 60 µL reaction.

All siRNA's showed a significant reduction in the PLOD2 expression. All siRNA's reduced the PLOD2 expression in human fibroblasts with 90% ($\Delta$Ct approximately 4 cycles) as shown in Tables 3 and 4, and FIG. 3.

TABLE 3

Results of 2 evaluation studies (#A and #B) on siRNA-based reduction of PLOD2 expression in fibroblasts.

| Sample | Replicates RT-PCR threshold cycles (Ct) | | | Average | Sd |
|---|---|---|---|---|---|
| 1A: siRNA #1 | 24.6 | 24.1 | 23.9 | 24.2 | 0.34 |
| 2A: siRNA #2 | 23.8 | 23.8 | 24.3 | 23.9 | 0.27 |
| 3A: siRNA #3 | 24.7 | 24.7 | 24.6 | 24.7 | 0.04 |
| 4A: control | 20.3 | 20.6 | 20.7 | 20.5 | 0.21 |
| 1B: siRNA #1 | 24.1 | 24.2 | 24.3 | 24.2 | 0.10 |
| 2B: siRNA #2 | 24.2 | 24.1 | 24.1 | 24.1 | 0.07 |
| 3B: siRNA #3 | 24.7 | 24.6 | 24.4 | 24.5 | 0.15 |
| 4B: control* | 20.7  20.2 | 20.8  20.4 | 0.37  19.8 | 20.4 | 0.37 |

*Control 4B was measured 6×; 3× as the undiluted standard and 3× as sample.

Results are expressed as number of RT-PCR threshold cycles. Compared to control, non-transfected fibroblasts the difference in threshold cycles ($\Delta$Ct)≈4 cycles.

TABLE 4

Results of 2 evaluation studies (#A and #B) on siRNA-based reduction of PLOD2 expression in fibroblasts.

| Sample | Average (relative expression %) | Standard deviation (relative expression %) |
|---|---|---|
| 1A: siRNA #1 | 9 | 2.02 |
| 2A: siRNA #2 | 11 | 1.86 |
| 3A: siRNA #3 | 7 | 0.16 |
| 4A: control | 108 | 16.25 |
| 1B: siRNA #1 | 9 | 0.60 |
| 2B: siRNA #2 | 10 | 0.45 |
| 3B: siRNA #3 | 7 | 0.74 |
| 4B: control | 122 | 30.52 |

Figure 3:
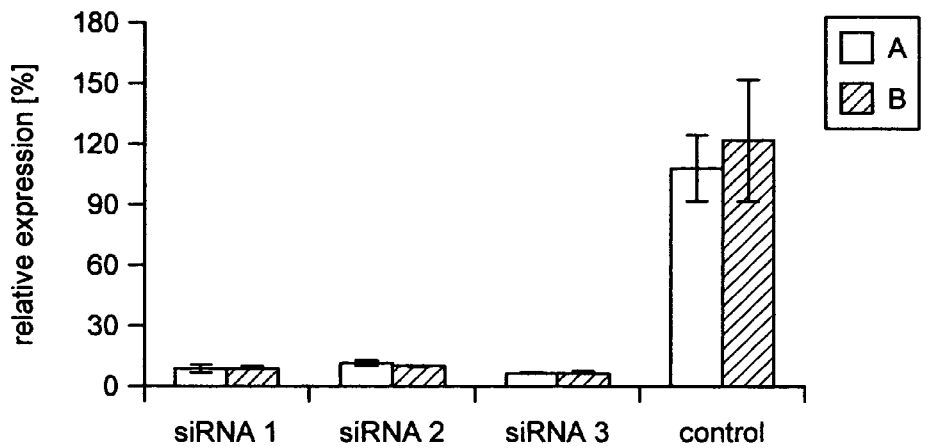
FIG. 3. Graphical representation of the results of 2 evaluation studies (#A and #B) on siRNA-based reduction of PLOD2 expression in human fibroblasts. Results are being expressed as percentage relative PLOD2 expression. Compared to control, non-transfected controls reduction of PLOD2 expression is 90%.

Results listed in Table 3 are transformed and expressed in Table 4 as a percentage (%) relative PLOD2 expression. Compared to control, non-transfected controls reduction of PLOD2 expression was 90%. FIG. 3 gives a graphical representation of the results listed in Tables 3 and 4.

To demonstrate that the anti-PLOD2 activity of the used siRNAs was a specific effect and did not induce an inhibitory effect on other enzymes involved in collagen synthesis, the three siRNA's were also tested in the same fibroblast cells for their effect on the following genes: LOX (lysyl oxidase) and COL1A2 (collagen type I, alpha 2). The results are shown in Tables 5 and 6.

TABLE 5

Effect of anti-PLOD2 siRNA's on LOX expression. Results of 2 independent evaluation studies (#A and #B).

| Sample | Replicates threshold cycles | | | Average | Sd |
|---|---|---|---|---|---|
| 1A: siRNA #1 | 18.8 | 18.7 | 18.1 | 18.8 | 0.12 |
| 2A: siRNA #2 | 19.4 | 19.2 | 19.6 | 19.4 | 0.22 |
| 3A: siRNA #3 | 19.2 | 19.2 | 19.2 | 19.2 | 0.02 |
| 4A: control | 19.2 | 18.6 | 18.9 | 18.9 | 0.27 |
| 1B: siRNA #1 | 18.8 | 19.2 | 17.9 | 19.0 | 0.33 |
| 2B: siRNA #2 | 19.3 | 19.2 | 19.2 | 19.2 | 0.06 |
| 3B: siRNA #3 | 19.3 | 18.8 | 18.8 | 19.0 | 0.27 |
| 4B: control | 19.1 | 18.9 | 18.9 | 19.0 | 0.10 |

The data presented in Table 5, shows that there was no significant difference in LOX expression due to siRNA treatment of the fibroblasts as can be derived from the fact that there is no difference observed in RT-PCR thresholds between the treatment and control groups.

TABLE 6

Effect of anti-PLOD2 siRNA's on COL1A2 expression. Results of 2 independent evaluation studies (#A and #B).

| Sample | Replicates threshold cycles | | | Average | Sd |
|---|---|---|---|---|---|
| 1A: siRNA #1 | 16.5 | 15.5 | 16.6 | 16.6 | 0.07 |
| 2A: siRNA #2 | 16.2 | 16.2 | 16.5 | 16.3 | 0.21 |
| 3A: siRNA #3 | 16.1 | 16.1 | 16.1 | 16.1 | 0.01 |
| 4A: control | 15.3 | 15.7 | 15.8 | 15.6 | 0.23 |
| 1B: siRNA #1 | 16.0 | 15.9 | 15.8 | 15.9 | 0.11 |
| 2B: siRNA #2 | 15.8 | 15.9 | 15.7 | 15.8 | 0.10 |
| 3B: siRNA #3 | 15.8 | 15.9 | 15.9 | 15.9 | 0.03 |
| 4B: control | 15.7 | 15.6 | 15.7 | 15.7 | 0.06 |

The data presented in Table 6, shows that there was no significant difference in COL1A2 expression due to siRNA treatment of the fibroblasts as can be derived from the fact that there is no difference observed in RT-PCR thresholds between the treatment and control groups.

Conclusion:

The expression of lysyl oxidase (LOX) and collagen, type I, alpha 2 (COL1A2) was not affected by the siRNA's targeting PLOD2. This confirms specificity of the 3 siRNA designs in hand for silencing of the PLOD2 gene.

Example 3 siRNA Specificity of PLOD2 Suppression in Human Fibroblasts

In this experiment three different siRNA designs were tested using human fibroblasts. Two siRNA designs, targeting PLOD2, ('siRNA #1' and 'siRNA #3') were previously demonstrated to strongly suppress PLOD2 expression. The third siRNA design ('scrambled') is a scrambled siRNA. The latter is included to verify specificity of the afore-determined siRNA-induced suppression of PLOD2. RNA isolated from transfected human fibroblasts was quantified using Real Time RT-PCR and compared with RNA isolated from non-transfected cells.

Materials & Methods:

```
siRNA #1:
sense sequence
5'GGUCCUUGGUCAAGGAGAAtt 3'      (SEQ ID NO:1)

anti-sense sequence
5'UUCUCCUUGACCAAGGACCtt 3'      (SEQ ID NO:2)

siRNA #3:
sense sequence
5'GGUACAAUUGCUCUAUUGAtt 3'      (SEQ ID NO:5)

anti-sense sequence
5'UCAAUAGAGCAAUUGUACCtt 3'      (SEQ ID NO:6)
``` scrambled: Scrambled siRNA was ordered at Ambion Inc. (catalog number 4611). Sequence is not known. The scrambled siRNA is claimed to have no homology to any known gene sequence from mouse, rat, or human.

Cell culture: Human fibroblasts (CCD-1077Sk cells, ATCC) were cultured in Iscoves modified Dulbecco's medium supplemented with 10% fetal bovine serum, 1% PSN antibiotics, 1% Fungizone antimycotics (Gibco) at 37° C. and 5% $CO_2$.

Transfection: $2\times10^5$ fibroblasts were plated in a 25 cm² culture flask containing 7 mL of growth medium without antibiotics one day before transfection so that they will be 50% confluent at the time of transfection. The cells were transfected with 840 pmol siRNA (final concentration: 100 nM) diluted in 700 μL Opti-MEM I using 14 μL Lipofectamine 2000 transfection reagent diluted in another 700 μL Opti-MEM I (Invitrogen). Growth medium was changed after 12 hours and RNA was isolated after 36 hours of incubation.

Semi-quantification: The cells were harvested from the culture flasks with 1 mL of Trypsin-EDTA (0.25% Trypsin, 1 mM EDTA•4Na, Gibco). Total RNA was isolated from the cells using the RNeasy mini kit (Qiagen) and gDNA was removed using an on column DNase treatment (30 min). After isolation, absence of gDNA was confirmed by a PCR using the MCP-1 primerset. The A260 was measured to correct for the amount of RNA. Reverse transcription took place using the iScript cDNA synthesis kit (Bio-Rad). Subsequently, two Real Time PCR's were carried out using iQ SYBR Green supermix (Bio-Rad), one with PLOD2 primerset and one with the GAPDH primerset which is used as internal control. The GAPDH standard curve was generated by amplifying the following numbers of DNA control molecules (in triple) in a 25 μL reaction: $1\times10^{10}$, $1\times10^9$, $1\times10^8$ ... to $1\times10^3$. The DNA control molecule was chemically synthesized (Life Technologies) and has the same sequence as the PCR product. The PLOD2 standard curve was made by amplifying the cDNA of an untransfected control sample undiluted, 10× diluted, 100× diluted and 1000× diluted. The undiluted sample was set at 100% expression the others at respectively 10%, 1%, and 0.1% expression.

Results:

Gel electrophoresis: The quality of the RNA was checked by gel electrophoresis. High quality RNA has two bands, the 28S rRNA band and the 18S rRNA band. For high quality RNA the intensity of these bands should be 2:1; this was indeed confirmed.

Control PCR: To confirm absence of gDNA a real time PCR was carried out using SYBR Green. Besides the positive control, one sample crossed the threshold and gave a significant signal. Since this occurred very late in the reaction (cycle 38), it was neglected as non-significant.

Reverse Transcriptase Reaction: All RNA samples were diluted to the same concentration before continuing with the RT-reaction. The entire 40 μL of diluted sample (3 μg RNA) was reverse transcribed in a 60 μL reaction.

Figure 4:
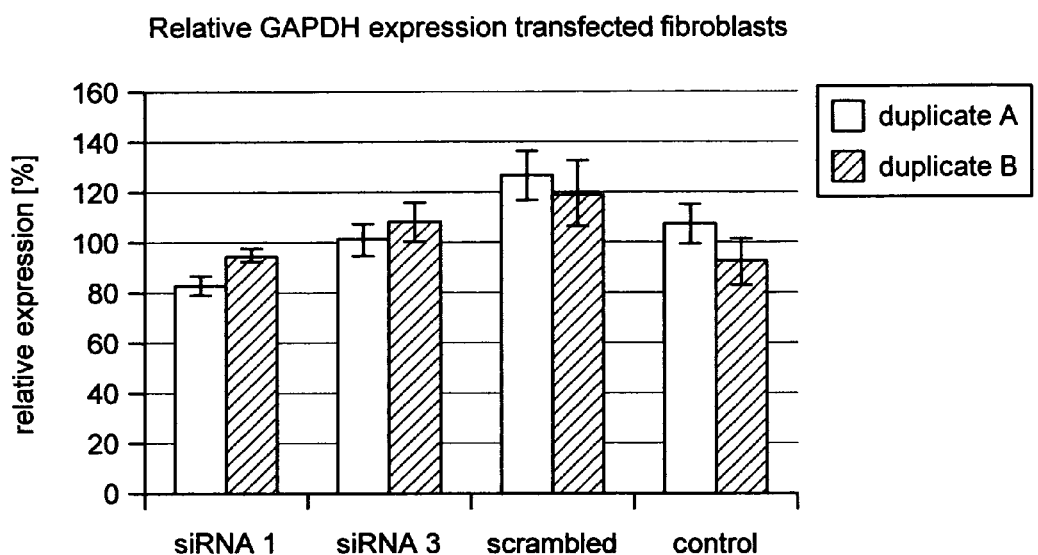
FIG. 4. Graphical representation of the results of a study using scrambled siRNA on expression of the housekeeping gene GAPDH in human fibroblasts.
Figure 5:
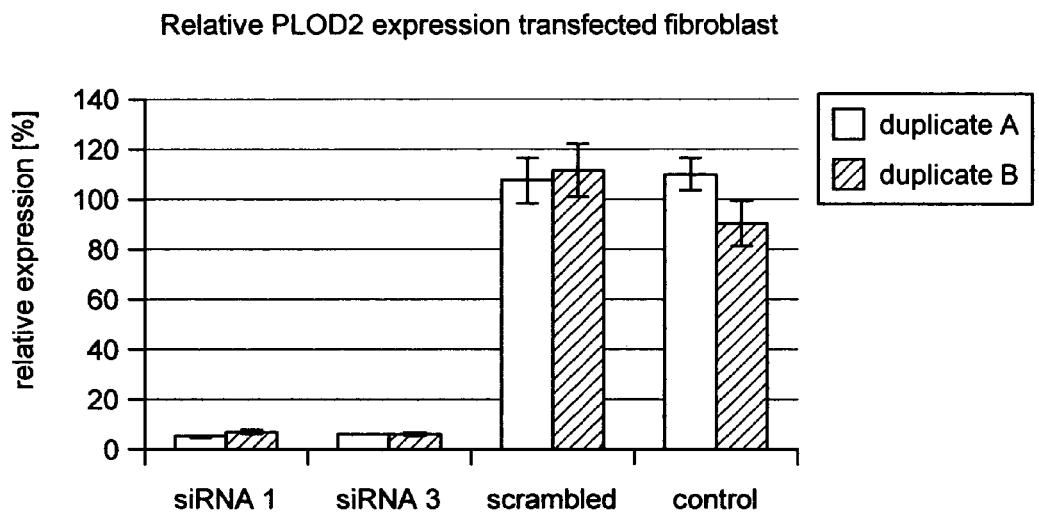
FIG. 5. Graphical representation of the results of a study using scrambled siRNA on PLOD2 expression in human fibroblasts.

The designed siRNA's showed a significant reduction in the PLOD2 expression. siRNA #1 and siRNA #3 reduced the PLOD2 expression in human fibroblasts with 90% (ΔCt approximately 4 cycles). In contrast, the scrambled siRNA design did not show any effect on PLOD2 expression, as shown in FIGS. 4 and 5.

Example 4

Quantification of PLOD 2 in Transfected Human Skin Fibroblasts

Materials & Methods:

```
siRNA #1:
sense sequence
5'GGUCCUUGGUCAAGGAGAAtt 3'      (SEQ ID NO:1)

anti-sense sequence
5'UUCUCCUUGACCAAGGACCtt 3'      (SEQ ID NO:2)

siRNA #2:
sense sequence
5'GGAGAAGAAUGGAGAGGUGtt 3'      (SEQ ID NO:3)

anti-sense sequence
5'CACCUCUCCAUUCUUCUCCtt 3'      (SEQ ID NO:4)

siRNA #3:
sense sequence
5'GGUACAAUUGCUCUAUUGAtt 3'      (SEQ ID NO:5)

anti-sense sequence
5'UCAAUAGAGCAAUUGUACCtt 3'      (SEQ ID NO:6)
```

Cell culture: Human fibroblasts (passage 10; donor 30/9) were isolated from skin tissue (Slot et al., *J. Biol. Chem.*, 278(42):40967-72 (2003)). Medium with 4500 milligrams per liter (mg/L) Glucose, pyruvate and glutamax (GIBCO, ref 31966-021) supplemented with 10% heat-inactivated fetal bovine serum, and 1% Penicilin/streptomycin. antibiotics at 37° C. and 5% $CO_2$.

Transfection: 2×10⁵ cells were plated in a 6-wells plate containing 3 mL of medium without antibiotics one day before transfection. At the time of transfection the cells were 80-90% confluent. The cells were transfected with 840 pmol siRNA or block-it fluorescent oligo (Invitrogen) in 3.4 mL medium (final concentration: 250 nM) using 14 μL Lipofectamine 2000 and 700 μL Opti-MEM I (Invitrogen). Medium was changed after 14 hours and RNA was isolated after 40 hours of incubation.

Quantification: Cells were washed with PBS and lysated with 350 μL RLT buffer. Total RNA (30 μl) was isolated using the RNeasy mini kit (catalog number 74106; Qiagen). RNA (8.2 μL) was reverse transcribed into 20 μL cDNA (First Strand cDNA Synthesis kit; Roche ref. 1483188), diluted 10 times with milli Q water and subjected to real-time PCR amplification. Real-time PCR amplification of cDNA sequences was performed on 10 μL diluted cDNA for Plod 1, 2b, 3, α2 chain of collagen type 1 (Col1A2), α1 chain of collagen type 3 (Col3A1), Lysyl Oxidase (Lox), Proline 4-hydroxylase I (P4HA-1) and β-2-microglobulin (B2M) to standardize for differences in the total amount of cDNA. Each cDNA was amplified using specific primers and specific molecular beacons (Slot et al., *J. Biol. Chem.*, 278(42):40967-72 (2003)) in a total reaction volume of 25 μL. PCR's were performed in an ABI PRISM 7700 sequence detection system and data were analyzed using sequence detector version 1.7 software.

Results:

TABLE 7

Real-time PCR data: Transfected human skin fibroblasts.

| | cycli | fmol | | cycli | fmol |
|---|---|---|---|---|---|
| B2M expression | | | PLOD2 expression | | |
| siRNA #1 a | 19.95 | 865.5 | siRNA #1 a | 27.18 | 26.8 |
| siRNA #1 b | 20.19 | 755.9 | siRNA #1 b | 28.01 | 17.3 |
| siRNA #2 a | 19.77 | 958.0 | siRNA #2 a | 26.3 | 42.7 |
| siRNA #2 b | 20.98 | 484.1 | siRNA #2 b | 28.25 | 15.3 |
| siRNA #3 a | 20.33 | 698.5 | siRNA #3 a | 28.54 | 13.1 |
| siRNA #3 b | 18.39 | 2086.9 | siRNA #3 b | 27.06 | 28.6 |
| control a | 19.07 | 1422.0 | control a | 22.11 | 388.6 |
| control b | 18.93 | 1538.8 | control b | 22.5 | 316.4 |
| GFP a | 19.15 | 1359.2 | GFP a | 22.47 | 321.5 |
| GFP b | 19.87 | 905.5 | GFP b | 23.04 | 238.0 |
| Col1A2 expression | | | Lysyl Oxidase (LOX) expression | | |
| siRNA #1 a | 17.23 | 4609.0 | siRNA #1 a | 18.82 | 3107.2 |
| siRNA #1 b | 17.86 | 3110.9 | siRNA #1 b | 19.46 | 2070.5 |
| siRNA #2 a | 17.01 | 5287.1 | siRNA #2 a | 18.25 | 4460.4 |
| siRNA #2 b | 17.63 | 3591.0 | siRNA #2 b | 19.31 | 2277.2 |
| siRNA #3 a | 17.84 | 3150.0 | siRNA #3 a | 19.24 | 2380.6 |
| siRNA #3 b | 17.01 | 5287.1 | siRNA #3 b | 18.15 | 4752.5 |
| control a | 16.47 | 7405.4 | control a | 17.41 | 7598.8 |
| control b | 16.44 | 7545.3 | control b | 17.21 | 8626.5 |
| GFP a | 16.69 | 6455.6 | GFP a | 17.95 | 5395.2 |
| GFP b | 17.47 | 3968.0 | GFP b | 18.61 | 3549.9 |
| Proline 4-Hydroxylase I (P4HA-1) expression | | | Col3A1 expression | | |
| siRNA #1 a | 21.33 | 31.9 | siRNA #1 a | 18.07 | 172.3 |
| siRNA #1 b | 21.27 | 33.0 | siRNA #1 b | 18.56 | 129.3 |
| siRNA #2 a | 20.43 | 55.1 | siRNA #2 a | 17.18 | 290.4 |
| siRNA #2 b | 21.34 | 31.7 | siRNA #2 b | 18.13 | 166.3 |
| siRNA #3 a | 21.8 | 23.9 | siRNA #3 a | 18.35 | 146.2 |
| siRNA #3 b | 21.98 | 21.5 | siRNA #3 b | 17.77 | 205.4 |
| control a | 20.39 | 56.4 | control a | 17.43 | 250.8 |
| control b | 20.2 | 63.3 | control b | 17.37 | 259.8 |
| GFP a | 20.77 | 44.8 | GFP a | 17.24 | 280.3 |
| GFP b | 20.48 | 53.4 | GFP b | 17.42 | 252.2 |

TABLE 7-continued

Real-time PCR data: Transfected human skin fibroblasts.

| | cycli | fmol | | cycli | fmol |
|---|---|---|---|---|---|
| PLOD1 expression | | | PLOD3 expression | | |
| siRNA #1 a | 23.26 | 22.1 | siRNA #1 a | 24.19 | 149.5 |
| siRNA #1 b | 23.6 | 16.9 | siRNA #1 b | 24.61 | 115.3 |
| siRNA #2 a | 22.78 | 32.4 | siRNA #2 a | 23.9 | 179.0 |
| siRNA #2 b | 23.62 | 16.6 | siRNA #2 b | 24.2 | 148.6 |
| siRNA #3 a | 24.15 | 10.9 | siRNA #3 a | 24.27 | 142.3 |
| siRNA #3 b | 23.2 | 23.2 | siRNA #3 b | 23.53 | 225.1 |
| control a | 23.25 | 22.3 | control a | 22.06 | 559.6 |
| control b | 23 | 27.2 | control b | 23.5 | 229.3 |
| GFP a | 22.45 | 42.1 | GFP a | 23.81 | 189.2 |
| GFP b | 23.04 | 26.3 | GFP b | 24.41 | 130.5 |

Figure 6A:
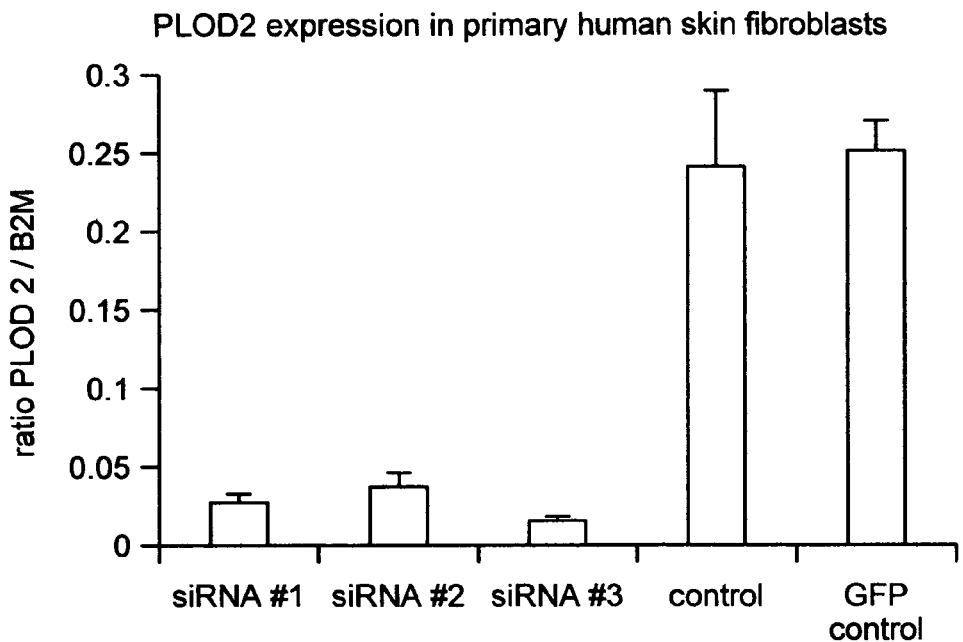
FIG. 6. 6A) Graphical representation of siRNA-based PLOD2 expression in relation to the housekeeping gene B2M in primary human skin fibroblasts. 6B) Graphical representation of siRNA-based COL1A2 expression in relation to the housekeeping gene B2M in primary human skin fibroblasts.
Figure 6B:
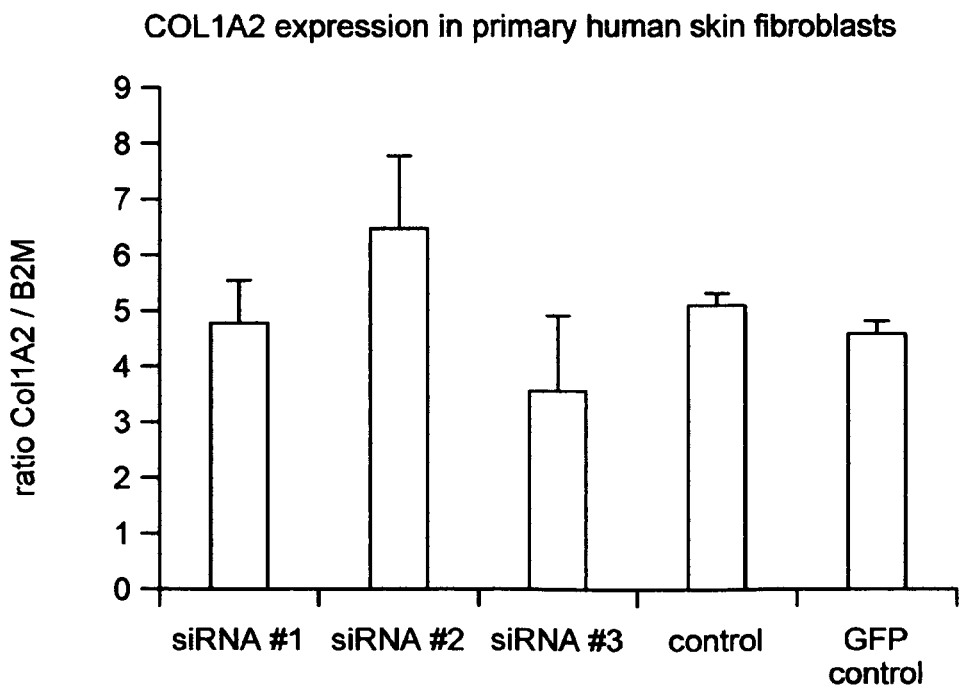
Figure 7A:
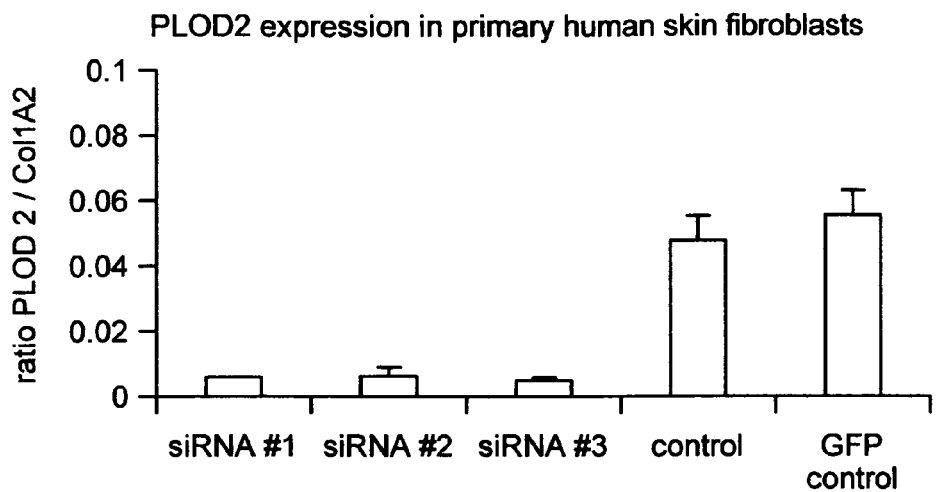
FIG. 7. 7A) Graphical representation of siRNA-based PLOD2 expression in relation to COL1A2 expression in primary human skin fibroblasts. 7B) Graphical representation of siRNA-based PLOD1 expression in relation to COL1A2 expression in primary human skin fibroblasts. 7C) Graphical representation of siRNA-based PLOD3 expression in relation to COL1A2 expression in primary human skin fibroblasts.
Figure 7B:
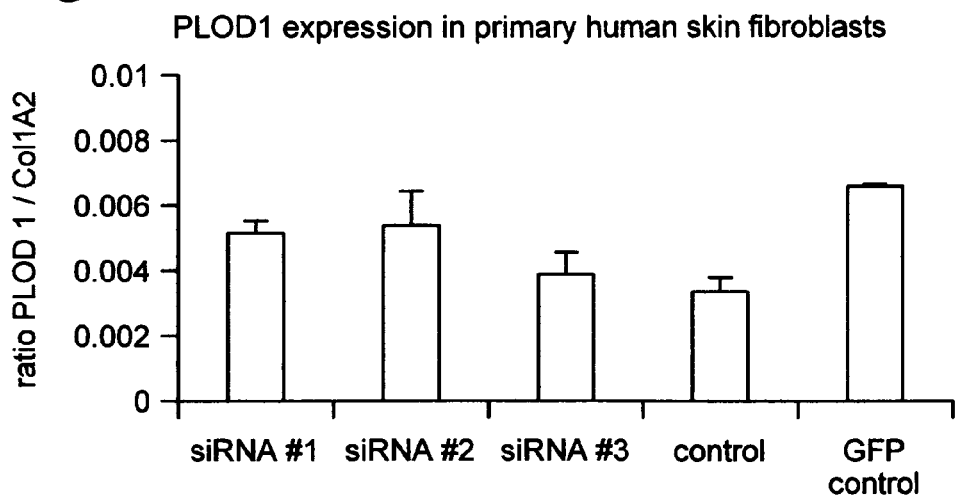
Figure 7C:
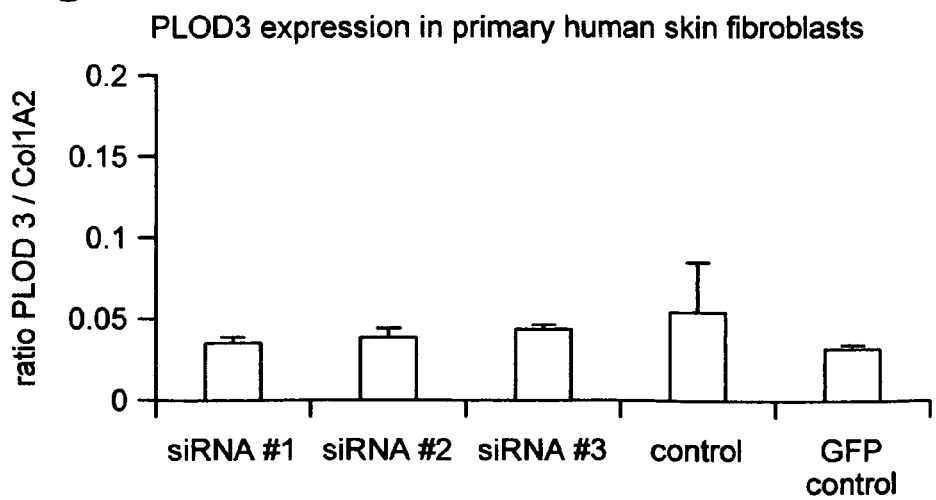

Also in the primary human skin fibroblast cells all siRNA's showed a significant reduction in the PLOD2 expression as can be seen in Table 7 and FIGS. 6 and 7. All siRNA's reduced the PLOD2 expression in human fibroblasts with 90% or more.

Figure 8A:
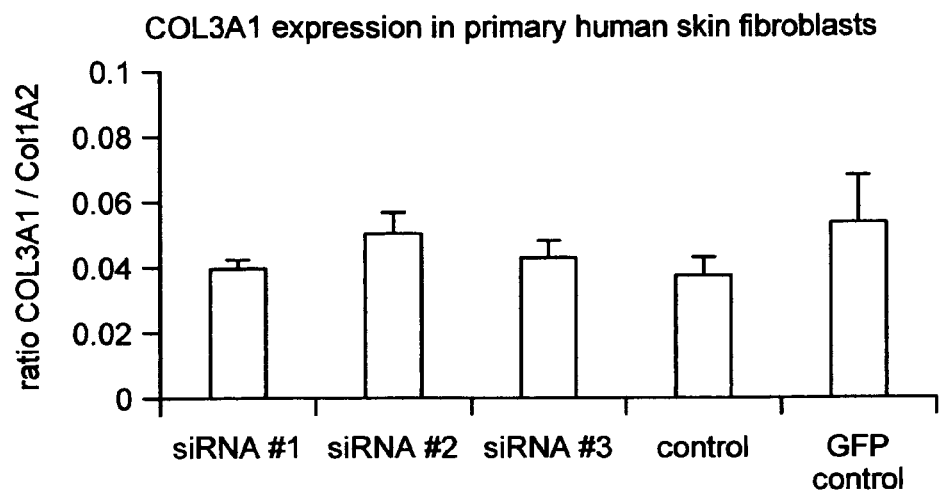
FIG. 8. 8A) Graphical representation of siRNA-based COL3A1 expression in relation to COL1A2 expression in primary human skin fibroblasts. 8B) Graphical representation of siRNA-based LOX expression in relation to COL1A2 expression in primary human skin fibroblasts. 8C) Graphical representation of siRNA-based P4HA-1 expression in relation to COL1A2 expression in primary human skin fibroblasts.
Figure 8B:
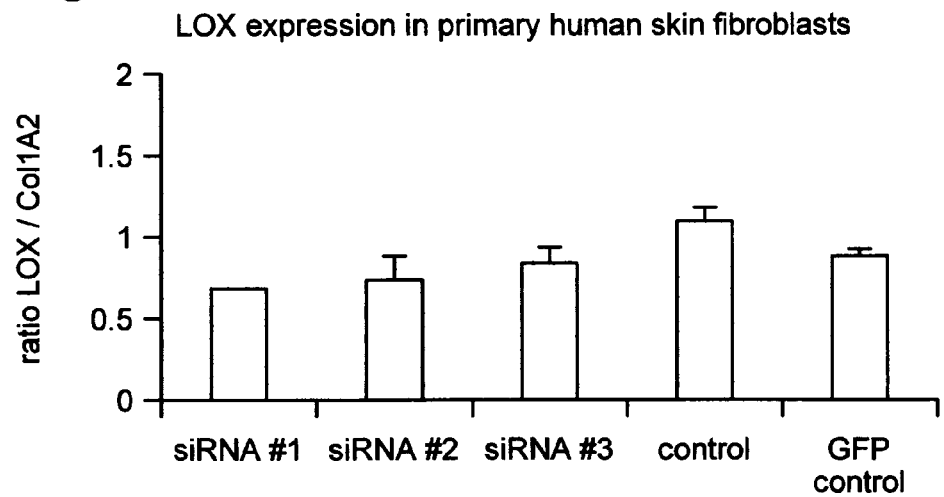
Figure 8C:
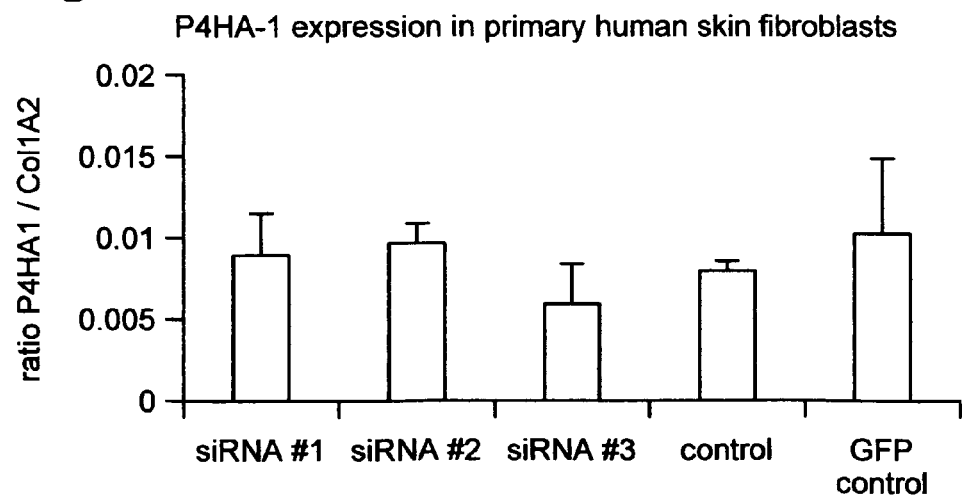
Figure 9A:
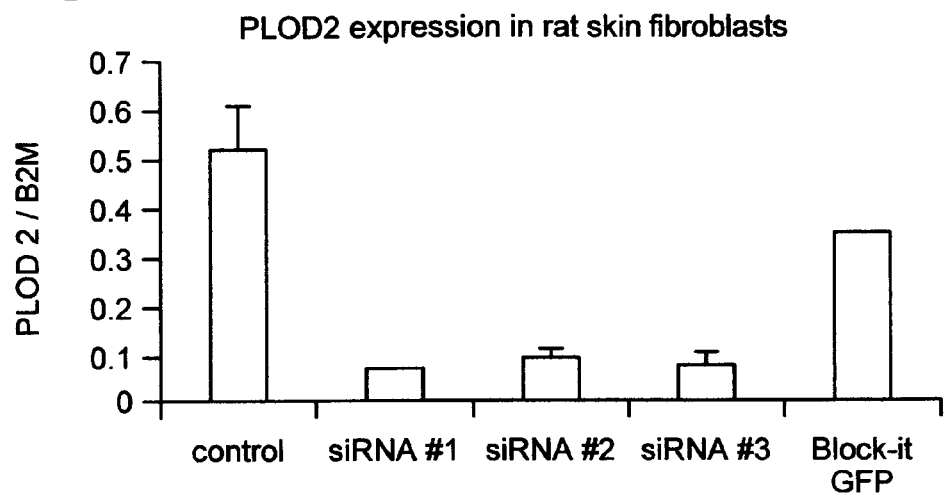
FIG. 9. 9A) Graphical representation of siRNA-based PLOD2 expression in relation to the housekeeping gene B2M in rat skin fibroblasts. 9B) Graphical representation of siRNA-based PLOD1 expression in relation to the housekeeping gene B2M in rat skin fibroblasts. 9C) Graphical representation of siRNA-based PLOD3 expression in relation to the housekeeping gene B2M in rat skin fibroblasts. 9D) Graphical representation of siRNA-based COL1A2 expression in relation to the housekeeping gene B2M in rat skin fibroblasts. 9E) Graphical representation of siRNA-based COL3A1 expression in relation to the housekeeping gene B2M in rat skin fibroblasts. 9F) Graphical representation of siRNA-based LOX expression in relation to the housekeeping gene B2M in rat skin fibroblasts. 9G) Graphical representation of siRNA-based P4HA-1 expression in relation to the housekeeping gene B2M in rat skin fibroblasts.
Figure 9B:
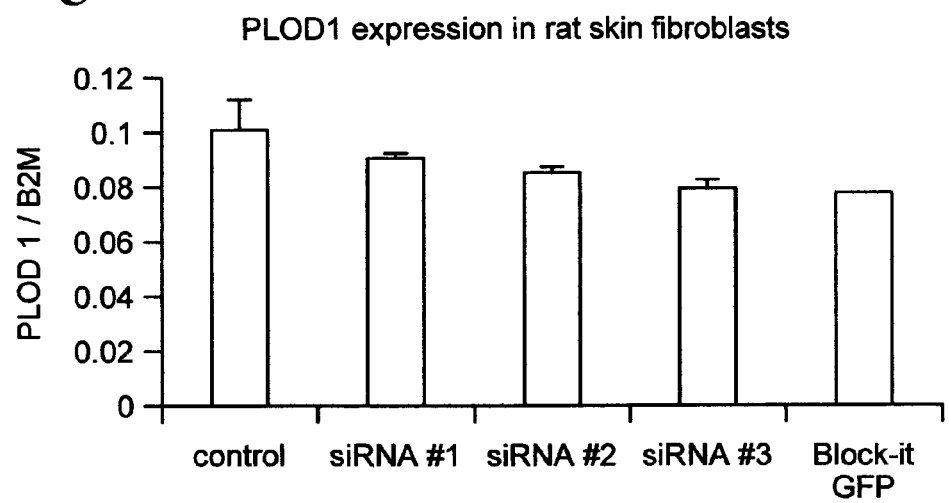
Figure 9C:
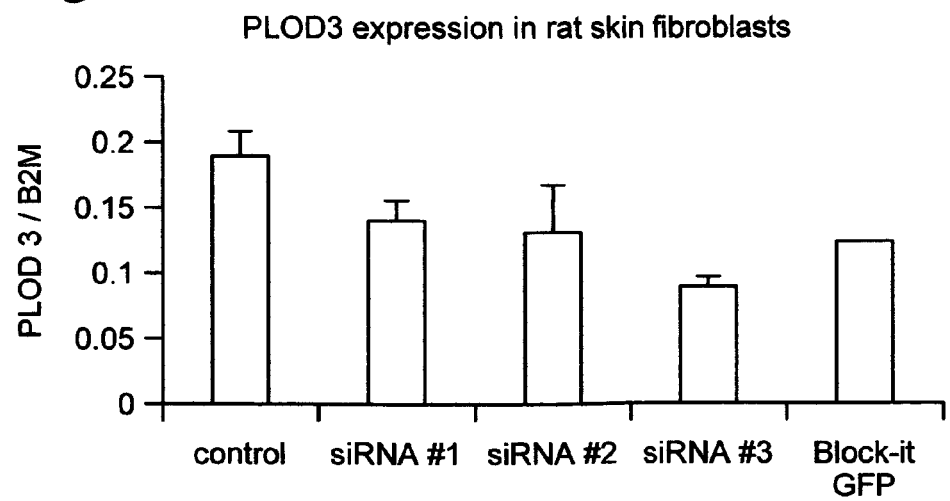
Figure 9D:
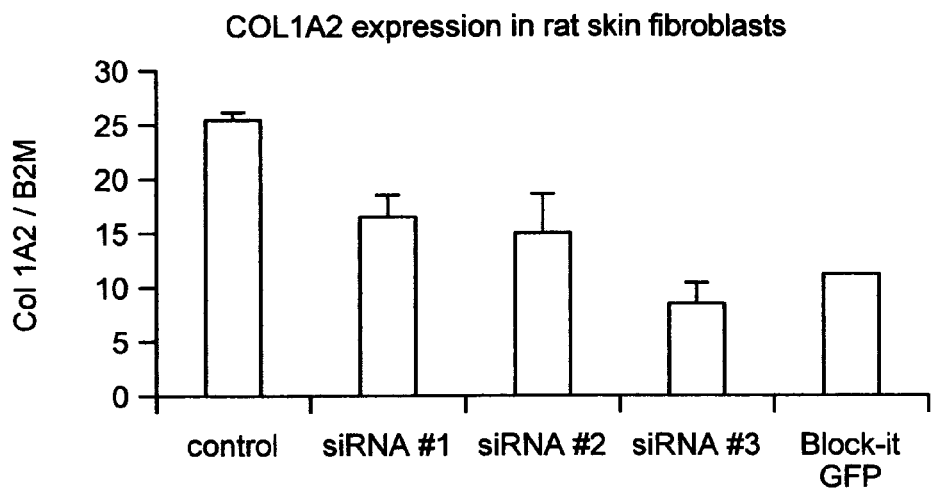
Figure 9E:
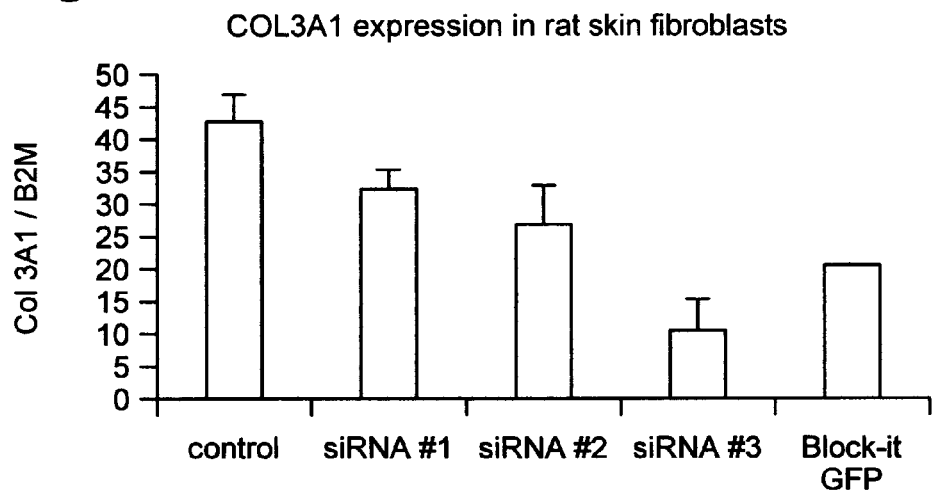
Figure 9F:
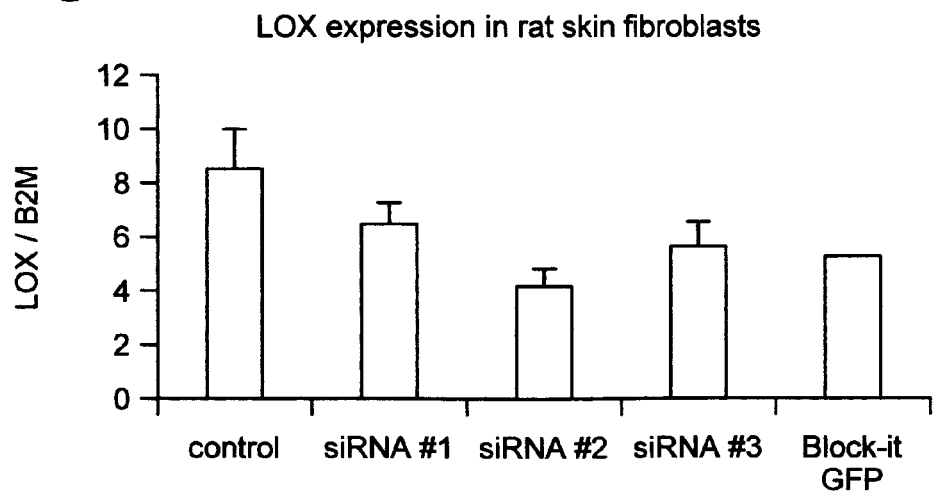
Figure 9G:
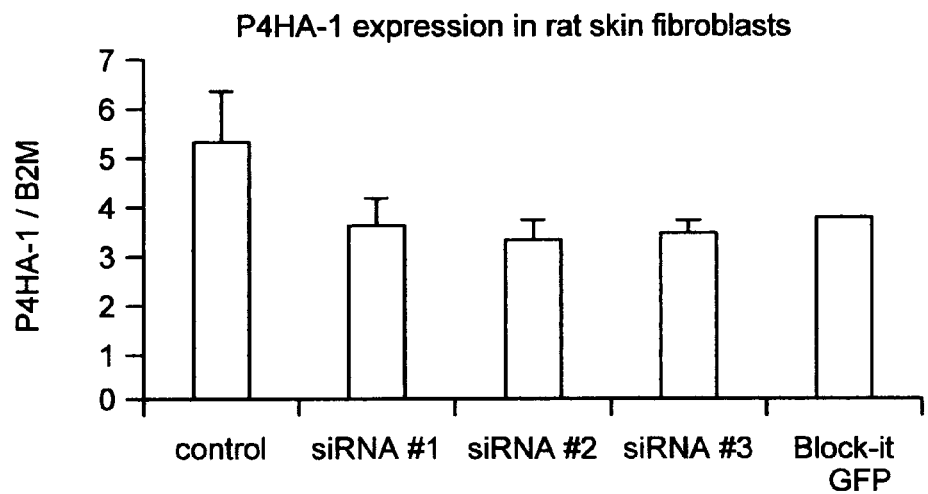
Figure 10A:
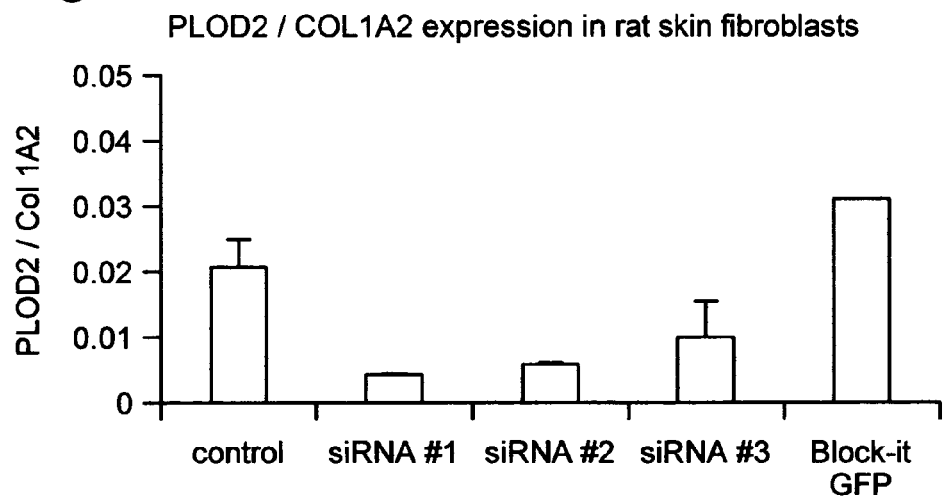
FIG. 10. 10A) Graphical representation of siRNA-based PLOD2 expression in relation to COL1A2 expression in rat skin fibroblasts. 10B) Graphical representation of siRNA-based PLOD1 expression in relation to COL1A2 expression in rat skin fibroblasts. 10C) Graphical representation of siRNA-based COL3A1 expression in relation to COL1A2 expression in rat skin fibroblasts. 10D) Graphical representation of siRNA-based LOX expression in relation to COL1A2 expression in rat skin fibroblasts. 10E) Graphical representation of siRNA-based P4HA-1 expression in relation to COL1A2 expression in rat skin fibroblasts.
Figure 10B:
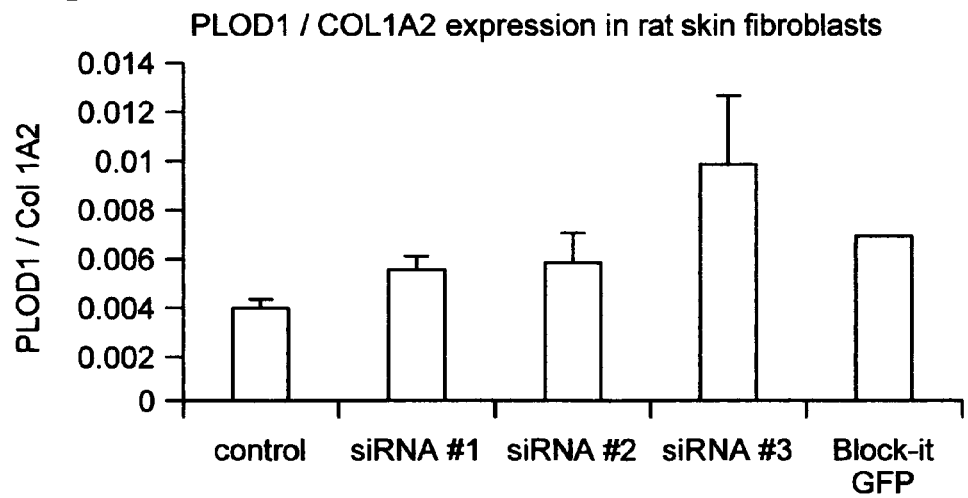
Figure 10C:
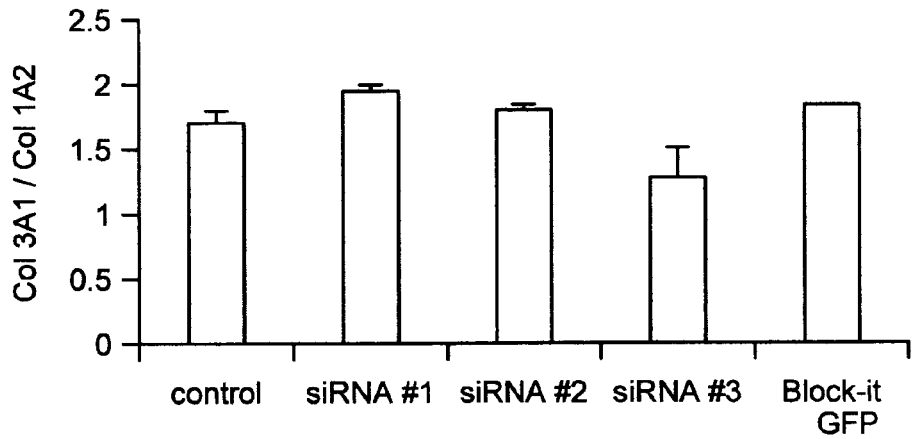
Figure 10D:
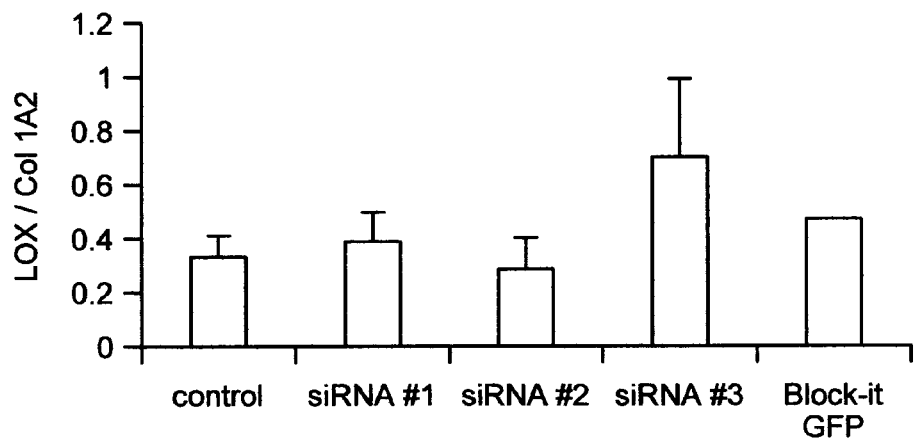
Figure 10E:
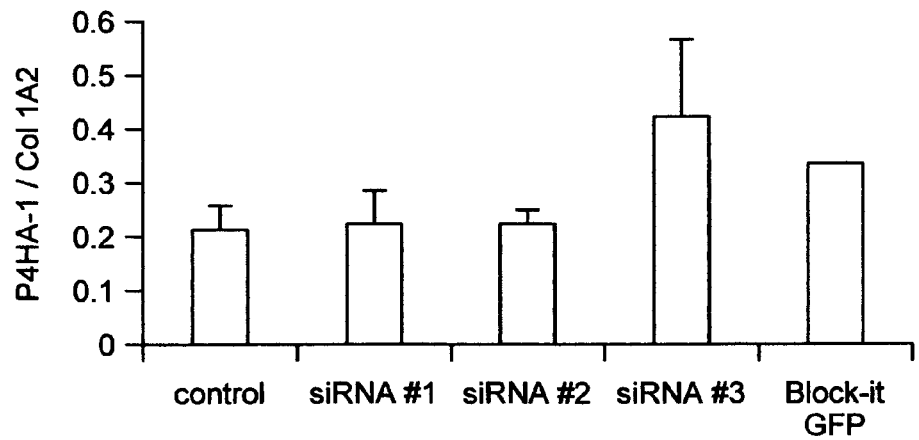

There was no significant difference in expression in any of the other genes due to siRNA treatment of the primary human skin fibroblasts as can be derived from the fact that there is no difference observed in RT-PCR threshold cycli between the treatment and control groups (Table 7 and FIGS. 6, 7, 8).

The results in FIGS. 6 and 7 demonstrate that siRNA induced suppression of PLOD2 does not interfere with the expression of COL1A2 nor any of the other collagen modifying enzymes.

Conclusion:

The effect of siRNA molecules on PLOD2 is very specific and is a promising new approach to prevent PLOD2-induced hydroxyallysine crosslinking of collagen.

Example 5

Quantification of PLOD 2 in Transfected Rat Skin Fibroblasts

The aim of this experiment is to test the performance of rat PLOD2 siRNA in rat fibroblasts.

Materials & Methods: siRNA were synthesized by Ambion Inc. siRNA sequences toward rat PLOD2:

```
Nr 1: siRNA ID:47463
Sense seq:
5' GCAGAUAAGUUAUUAGUCAtt 3'    (SEQ ID NO:7)

Anti-sense
5' UGACUAAUAACUUAUCUGCtg 3'    (SEQ ID NO:8)

Nr 2: siRNA ID:47549
Sense seq:
5' GAAAACGAUGGAUUCCACAtt 3'    (SEQ ID NO:9)

Anti-sense
5' UGUGGAAUCCAUCGUUUUCtt 3'    (SEQ ID NO:10)

Nr 3: siRNA ID:47630
Sense seq:
5' GAUUUAUGAAUUCAGCCAAtt 3'    (SEQ ID NO:11)

Anti-sense
5' UUGGCUGAAUUCAUAAAUCtg 3'    (SEQ ID NO:12)
```

Cell culture: Rat fibroblasts (passage +6; ATCC 1213-CRL) were cultured in DMEM medium with 4500 milligrams per liter (mg/L) glucose, pyruvate and glutamax (GIBCO No.

31966-021) supplemented with 10% heat-inactivated fetal bovine serum, and 1% penicillin/streptomycin antibiotics at standard culture conditions (polystyrene culture wells; 37° C.; 5% $CO_2$).

Transfection: $5 \times 10^5$ cells were plated in a 6-wells plate containing 3 mL of medium without antibiotics one day before transfection. At the time of transfection the cells were 80-90% confluent. The cells were transfected with 840 pmol siRNA or block-it fluorescent oligo (Invitrogen) in 3.4 mL medium (final concentration: 250 nanomolar (nM)) using 14 µL Lipofectamine 2000 and 700 µL Opti-MEM I (Invitrogen). Medium was changed after 8 hours and RNA was isolated after 40 hours of incubation.

Quantification: Cells were washed with PBS and lysated with 350 µL RLT buffer. Total RNA (30 µL) was isolated using the RNeasy mini kit (Qiagen No. 74106). RNA (8.2 µL) was reverse transcribed into 20 µL cDNA (First Strand cDNA Synthesis kit; Roche No. 1483188), diluted 10 times with Milli-Q water and subjected to real-time PCR amplification. Real-time PCR amplification of cDNA sequences was performed on 10 µL diluted cDNA for PLOD 1, 2, 3, the α2-chain of collagen type I (Col1A2), the α1-chain of collagen type III (Col3A1), lysyl oxidase (LOX), prolyl4-hydroxylase 1 (P4HA1) and β2-microglobulin (B2M). The latter gene was used to standardize for differences in the total amount of cDNA. Each cDNA was amplified using specific primers and specific molecular beacons (designed for the rat genes) in a total reaction volume of 25 µL. Real-time PCR reactions were performed in an ABI PRISM 7700 sequence detection system and data were analyzed using Sequence detector version 1.7 software.

Results:

TABLE 8

Real-time PCR data: Transfected rat skin fibroblasts.

| Rat B2M | cycli | cycli | fmol | fmol | mean | Rat PLOD 3 | cycli | cycli | fmol | fmol | mean |
|---|---|---|---|---|---|---|---|---|---|---|---|
| control a | 19.36 | 18.90 | 1091.98 | 1462.34 | 1277.16 | control a | 18.34 | 18.72 | 253.94 | 198.61 | 226.27 |
| control b | 19.59 | 19.32 | 943.62 | 1120.06 | 1031.84 | control b | 18.55 | 18.75 | 221.69 | 194.79 | 208.24 |
| siRNA nr 1a | 19.93 | 19.65 | 760.42 | 908.35 | 834.38 | siRNA nr 1a | 19.78 | 19.59 | 100.07 | 113.15 | 106.61 |
| siRNA nr 1b | 19.75 | 19.30 | 852.47 | 1134.38 | 993.43 | siRNA nr 1b | 19.12 | 19.20 | 153.34 | 145.61 | 149.47 |
| siRNA nr 2a | 19.56 | 19.29 | 961.77 | 1141.60 | 1051.68 | siRNA nr 2a | 19.12 | 18.91 | 153.34 | 175.65 | 164.49 |
| siRNA nr 2b | 19.42 | 18.92 | 1051.16 | 1443.89 | 1247.53 | siRNA nr 2b | 19.53 | 19.24 | 117.63 | 141.89 | 129.76 |
| siRNA nr 3a | 18.80 | 18.96 | 1558.19 | 1407.68 | 1482.93 | siRNA nr 3a | 19.66 | 19.20 | 108.14 | 145.61 | 126.87 |
| siRNA nr 3b | 19.49 | 19.26 | 1005.47 | 1163.55 | 1084.51 | siRNA nr 3b | 20.10 | 19.49 | 81.36 | 120.71 | 101.03 |
| block-it GFP | 18.62 | 18.45 | 1746.83 | 1945.91 | 1846.37 | block-it GFP | 18.58 | 18.46 | 217.43 | 234.98 | 226.20 |
| Rat PLOD 2 | cycli | cycli | fmol | fmol | mean | Rat Col 3A1 | cycli | cycli | fmol | fmol | mean |
| control a | 20.54 | 20.86 | 651.48 | 521.14 | 586.31 | control a | 15.31 | 15.49 | 62295.91 | 54009.07 | 58152.49 |
| control b | 20.69 | 20.63 | 586.76 | 611.84 | 599.30 | control b | 15.93 | 15.74 | 38100.31 | 44296.10 | 41198.21 |
| siRNA nr 1a | 24.03 | 24.12 | 57.09 | 53.62 | 55.35 | siRNA nr 1a | 16.29 | 16.66 | 28638.01 | 21355.66 | 24996.84 |
| siRNA nr 1b | 24.10 | 23.62 | 54.37 | 75.99 | 65.18 | siRNA nr 1b | 16.06 | 16.07 | 34368.13 | 34096.66 | 34232.40 |
| siRNA nr 2a | 23.09 | 23.18 | 109.99 | 103.30 | 106.64 | siRNA nr 2a | 16.09 | 16.16 | 33560.14 | 31747.93 | 32654.04 |
| siRNA nr 2b | 23.35 | 23.29 | 91.74 | 95.67 | 93.71 | siRNA nr 2b | 16.20 | 16.43 | 30756.67 | 25628.67 | 28192.67 |
| siRNA nr 3a | 23.06 | 22.49 | 112.32 | 167.16 | 139.74 | siRNA nr 3a | 17.51 | 17.44 | 10883.51 | 11504.75 | 11194.13 |
| siRNA nr 3b | 23.99 | 24.09 | 58.71 | 54.75 | 56.73 | siRNA nr 3b | 16.98 | 17.18 | 16569.27 | 14139.12 | 15354.20 |
| block-it GFP | 20.62 | 20.52 | 616.12 | 660.63 | 638.38 | block-it GFP | 15.92 | 15.96 | 38403.66 | 37204.58 | 37804.12 |
| Rat Col1A2 | cycli | cycli | fmol | fmol | mean | Rat LOX | cycli | cycli | fmol | fmol | mean |
| control a | 14.71 | 14.86 | 34775.71 | 31160.20 | 32967.96 | control a | 18.84 | 18.67 | 9091.09 | 10082.82 | 9586.95 |
| control b | 15.21 | 15.07 | 24118.86 | 26721.09 | 25419.98 | control b | 18.59 | 18.85 | 10586.26 | 9035.88 | 9811.07 |
| siRNA nr 1a | 15.93 | 16.29 | 14240.10 | 10941.86 | 12590.98 | siRNA nr 1a | 19.58 | 19.55 | 5792.69 | 5899.51 | 5846.10 |
| siRNA nr 1b | 15.42 | 15.87 | 20682.87 | 14879.33 | 17781.10 | siRNA nr 1b | 19.40 | 19.81 | 6463.86 | 5035.51 | 5749.68 |
| siRNA nr 2a | 15.55 | 15.59 | 18805.80 | 18263.25 | 18534.53 | siRNA nr 2a | 20.46 | 20.02 | 3389.33 | 4430.95 | 3910.14 |
| siRNA nr 2b | 15.89 | 15.75 | 14663.13 | 16245.16 | 15454.14 | siRNA nr 2b | 19.60 | 19.62 | 5722.56 | 5653.27 | 5687.92 |
| siRNA nr 3a | 16.40 | 16.38 | 10095.53 | 10244.38 | 10169.95 | siRNA nr 3a | 18.68 | 18.97 | 10021.60 | 8399.04 | 9210.32 |
| siRNA nr 3b | 16.31 | 16.34 | 10782.87 | 10548.71 | 10665.79 | siRNA nr 3b | 19.60 | 19.81 | 5722.56 | 5035.51 | 5379.04 |
| block-it GFP | 15.42 | 15.43 | 20682.87 | 20532.05 | 20607.46 | block-it GFP | 18.91 | 18.59 | 8711.65 | 10586.26 | 9648.95 |
| Rat PLOD 1 | cycli | cycli | fmol | fmol | mean | Rat P4HA-1 | cycli | cycli | fmol | fmol | mean |
| control a | 20.60 | 20.02 | 108.25 | 168.98 | 138.61 | control a | 20.10 | 20.30 | 6230.70 | 5569.71 | 5900.20 |
| control b | 20.58 | 21.00 | 109.92 | 79.62 | 94.77 | control b | 20.06 | 20.15 | 6372.02 | 6058.44 | 6215.23 |
| siRNA nr 1a | 20.90 | 21.30 | 85.98 | 63.24 | 74.61 | siRNA nr 1a | 21.48 | 21.00 | 2873.94 | 3761.56 | 3317.75 |
| siRNA nr 1b | 20.94 | 20.73 | 83.38 | 97.97 | 90.67 | siRNA nr 1b | 21.13 | 21.42 | 3497.12 | 2972.28 | 3234.70 |
| siRNA nr 2a | 20.81 | 20.85 | 92.13 | 89.34 | 90.74 | siRNA nr 2a | 21.12 | 20.89 | 3516.78 | 4000.88 | 3758.83 |
| siRNA nr 2b | 20.64 | 20.68 | 104.97 | 101.80 | 103.39 | siRNA nr 2b | 21.30 | 20.81 | 3179.16 | 4184.44 | 3681.80 |
| siRNA nr 3a | 20.31 | 20.63 | 135.25 | 105.78 | 120.51 | siRNA nr 3a | 20.57 | 20.19 | 4787.20 | 5924.06 | 5355.63 |
| siRNA nr 3b | 20.92 | 20.95 | 84.67 | 82.74 | 83.70 | siRNA nr 3b | 21.28 | 21.03 | 3215.01 | 3698.81 | 3456.91 |
| block-it GFP | 20.40 | 20.11 | 126.22 | 157.69 | 141.95 | block-it GFP | 20.04 | 19.80 | 6443.89 | 7372.13 | 6908.01 |

In rat skin fibroblasts PLOD2 expression is strongly suppressed with all three siRNA's oligonucleotides as can be seen in Table 8 and FIGS. 9 and 10.

Conclusion:

There is a good suppression of mRNA levels of PLOD2 with all three siRNA sequences. The siRNA has no effects on mRNA levels of PLOD1, PLOD3, lysyl oxidase (LOX), prolyl-4-hydroxylase-1 (P4HA-1), collagen type I (COL1A2) and collagen type III (COL3A1).

The complete disclosures of all patents, patent applications, publications, and nucleic acid and protein database entries, including for example GenBank accession numbers and EMBL accession numbers, that are cited herein are hereby incorporated by reference as if individually incorporated. Various modifications and alterations of this invention will become apparent to those skilled in the art without departing from the scope and spirit of this invention, and it should be understood that this invention is not to be unduly limited to the illustrative embodiments set forth herein.

What is claimed is:

1. A medical device comprising:
a substrate; and
an active agent associated with the substrate, wherein the active agent suppresses the production and/or activity of a TLH enzyme in collagen-producing cells and comprises a siRNA molecule or a DNA that encodes a siRNA molecule, wherein the siRNA molecule inhibits translation of a TLH enzyme and comprises one or more of SEQ ID NO:1, SEQ ID NO:2, SEQ ID NO:5, and SEQ ID NO:6.

2. The medical device of claim 1 which is an implantable device.

3. The medical device of claim 1 which is an extracorporeal device.

4. The medical device of claim 1 selected from the group consisting of a stent, stent graft, anastomotic connector, lead, needle, guide wire, catheter, sensor, surgical instrument, angioplasty balloon, wound drain, shunt, tubing, urethral insert, pellet, implant, blood oxygenator, pump, vascular graft, vascular access port, valve, suture, surgical clip, surgical staple, pacemaker, orthopedic device, replacement device for nucleus pulposus, and intraocular lens.

5. The medical device of claim 1 wherein the substrate comprises a polynucleotide delivery matrix.

6. A method for delivering an active agent to a subject, the method comprising:
providing a medical device comprising:
a substrate; and
an active agent associated with the substrate, wherein the active agent suppresses the production and/or activity of a TLH enzyme in collagen-producing cells and comprises a siRNA molecule or a DNA that encodes a siRNA molecule, wherein the siRNA molecule inhibits translation of a TLH enzyme and comprises one or more of SEQ ID NO:1, SEQ ID NO:2, SEQ ID NO:5, and SEQ ID NO:6; and
placing the medical device in the subject in contact with collagen-producing cells.

7. The method of claim 6 wherein the medical device is an implantable device.

8. The method of claim 6 wherein the medical device is an extracorporeal device.

9. The method of claim 6 wherein the medical device is selected from the group consisting of a stent, stent graft, anastomotic connector, lead, needle, guide wire, catheter, sensor, surgical instrument, angioplasty balloon, wound drain, shunt, tubing, uretbral insert, pellet, implant, blood oxygenator, pump, vascular graft, vascular access port, valve, suture, surgical clip, surgical staple, pacemaker, orthopedic device, replacement device for nucleus pulposus, and intraocular lens.

10. The method of claim 6 wherein the substrate comprises a polynucleotide delivery matrix.

11. A medical device embedded in a matrix that includes an active agent, wherein the active agent suppresses the production and/or activity of a TLH enzyme in collagen-producing cells and comprises a siRNA molecule or a DNA that encodes a siRNA molecule, wherein the siRNA molecule inhibits translation of a TLH enzyme and comprises one or more of SEQ ID NO:1, SEQ ID NO:2, SEQ ID NO:5, and SEQ ID NO:6.

12. The medical device of claim 11 wherein the matrix that includes the active agent is a polynucleotide delivery matrix.

13. The medical device of claim 12 wherein the polynucleotide delivery matrix comprises DNA encoding a siRNA molecule that interferes with a PLOD2 gene and inhibits the translation of a TLH enzyme.

14. The medical device of claim 12 wherein the polynucleotide delivery matrix comprises siRNA molecules that interfere with a PLOD2 gene and inhibit the translation of a TLH enzyme.

15. The medical device of claim 5 wherein the polynucleotide delivery matrix comprises DNA encoding a siRNA molecule that interferes with a PLOD2 gene mRNA and inhibits translation of a TLH enzyme.

16. A polynucleotide comprising a siRNA molecule or a DNA encoding a siRNA molecule, wherein the siRNA molecule comprises SEQ ID NO:1, SEQ ID NO:2, SEQ ID NO:5, or SEQ ID NO:6.

* * * * *

UNITED STATES PATENT AND TRADEMARK OFFICE
CERTIFICATE OF CORRECTION

| | | |
|---|---|---|
| PATENT NO. | : 7,767,652 B2 | |
| APPLICATION NO. | : 11/183485 | |
| DATED | : August 3, 2010 | |
| INVENTOR(S) | : Marc Hendriks | |

It is certified that error appears in the above-identified patent and that said Letters Patent is hereby corrected as shown below:

Col. 24, line 18, ...urethral insert... should read ..urethral insert,...

Signed and Sealed this
Twenty-first Day of February, 2012

David J. Kappos
*Director of the United States Patent and Trademark Office*